United States Patent
Smith et al.

(10) Patent No.: US 12,338,428 B2
(45) Date of Patent: Jun. 24, 2025

(54) MATERIALS AND METHODS FOR MANAGING AEROBIC GAS FERMENTATION

(71) Applicant: INV NYLON CHEMICALS AMERICAS, LLC, Wilmington, DE (US)

(72) Inventors: Gary J. Smith, North Yorkshire (GB); Paul S. Pearlman, Thornton, PA (US); Gregory S. Kirby, Avondale, PA (US)

(73) Assignee: INV NYLON CHEMICALS AMERICAS, LLC

(*) Notice: Subject to any disclaimer, the term of this patent is extended or adjusted under 35 U.S.C. 154(b) by 0 days.

(21) Appl. No.: 16/372,092

(22) Filed: Apr. 1, 2019

(65) Prior Publication Data

US 2019/0300838 A1 Oct. 3, 2019

Related U.S. Application Data

(60) Provisional application No. 62/650,575, filed on Mar. 30, 2018.

(51) Int. Cl.
| | |
|---|---|
| *C12N 1/20* | (2006.01) |
| *C12M 1/00* | (2006.01) |
| *C12M 1/04* | (2006.01) |
| *C12M 1/107* | (2006.01) |
| *C12M 1/34* | (2006.01) |
| *C12M 1/36* | (2006.01) |
| *C12P 1/00* | (2006.01) |
| *C12P 5/00* | (2006.01) |

(52) U.S. Cl.
CPC ............ *C12M 41/34* (2013.01); *C12M 1/04* (2013.01); *C12M 21/04* (2013.01); *C12M 23/58* (2013.01); *C12M 29/24* (2013.01); *C12M 41/48* (2013.01); *C12P 1/00* (2013.01); *C12P 5/00* (2013.01)

(58) Field of Classification Search
CPC ........ C12N 1/20; C12N 2500/02; C12R 1/01; C12R 1/06
See application file for complete search history.

(56) References Cited

U.S. PATENT DOCUMENTS

| | | |
|---|---|---|
| 3,957,876 A | 5/1976 | Rapoport et al. |
| 4,554,101 A | 11/1985 | Hopp |
| 6,207,217 B1 | 3/2001 | Peoples et al. |
| 6,888,034 B1 | 5/2005 | Landray et al. |
| 7,384,783 B2 | 6/2008 | Kunas et al. |
| 8,603,518 B2 | 12/2013 | Boon et al. |
| 8,809,027 B1 | 8/2014 | Lynch et al. |
| 8,986,960 B2 | 3/2015 | Sichwart |
| 9,221,737 B2 | 12/2015 | Valdez |
| 9,580,733 B2 | 2/2017 | Botes et al. |
| 9,637,764 B2 | 5/2017 | Botes et al. |
| 9,650,653 B2 | 5/2017 | Pearlman et al. |
| 9,862,973 B2 | 1/2018 | Botes et al. |
| 9,920,339 B2 | 3/2018 | Kadi et al. |
| 10,072,150 B2 | 9/2018 | Conradie et al. |
| 10,196,657 B2 | 2/2019 | Pearlman et al. |
| 10,577,634 B2 | 3/2020 | Pearlman et al. |
| 10,975,363 B2 | 4/2021 | Foster et al. |
| 2002/0192786 A1 | 12/2002 | Yamada et al. |
| 2005/0181499 A1 | 8/2005 | Brahmbhatt |
| 2007/0264688 A1 | 11/2007 | Venter et al. |
| 2007/0269862 A1 | 11/2007 | Glass et al. |
| 2010/0120104 A1 | 5/2010 | Reed |
| 2010/0167371 A1 | 7/2010 | Chotani et al. |
| 2011/0125118 A1 | 5/2011 | Lynch |
| 2011/0171702 A1 | 7/2011 | Reinecke et al. |
| 2012/0003706 A1 | 1/2012 | Hickey |
| 2012/0064622 A1 | 3/2012 | Fischer et al. |
| 2012/0295334 A1 | 11/2012 | Brahmbhatt |
| 2013/0034884 A1 | 2/2013 | Burgard et al. |
| 2013/0065285 A1 | 3/2013 | Sefton |
| 2013/0177957 A1 | 7/2013 | Du et al. |
| 2013/0189763 A1 | 7/2013 | Dalla-betta et al. |
| 2013/0323714 A1 | 12/2013 | Cheng et al. |
| 2014/0248687 A1 | 9/2014 | Kelly et al. |
| 2014/0330398 A1* | 11/2014 | Fan .................. C12M 41/34 700/20 |
| 2015/0132815 A1 | 5/2015 | Hickey |
| 2015/0315599 A1 | 11/2015 | Shetty et al. |
| 2016/0176813 A1 | 6/2016 | Valdez |
| 2017/0107474 A1 | 4/2017 | Farmer et al. |
| 2017/0159082 A1 | 6/2017 | Conradie et al. |
| 2017/0218406 A1 | 8/2017 | Conradie et al. |
| 2018/0023088 A1 | 1/2018 | Van Eck Conradie et al. |
| 2018/0023103 A1 | 1/2018 | Foster et al. |

(Continued)

FOREIGN PATENT DOCUMENTS

| | | |
|---|---|---|
| CN | 1735691 A | 2/2006 |
| CN | 102459579 A | 5/2012 |

(Continued)

OTHER PUBLICATIONS https://www.clrblu.com/aeration/ , "Aeration" (Year: 2021).*

(Continued)

*Primary Examiner* — Ruth A Davis

(57) ABSTRACT

Disclosed are materials and methods for managing aerobic biosynthesis. The materials include a fermenter system comprising a fermenter, a microorganism provided to the fermenter, and at least two control loops. The methods are directed to measuring and controlling different oxygen concentrations within the fermenter.

10 Claims, 6 Drawing Sheets

(56) References Cited

U.S. PATENT DOCUMENTS

| | | |
|---|---|---|
| 2018/0023104 A1 | 1/2018 | Cartman et al. |
| 2018/0100160 A1 | 4/2018 | Bawdon et al. |
| 2018/0327705 A1 | 11/2018 | Matsuka et al. |
| 2019/0124947 A1 | 5/2019 | Pearlman et al. |
| 2019/0300839 A1 | 10/2019 | Smith et al. |
| 2019/0316072 A1 | 10/2019 | Smith et al. |
| 2019/0338320 A1 | 11/2019 | Foster et al. |
| 2019/0352674 A1 | 11/2019 | Foster et al. |
| 2019/0352682 A1 | 11/2019 | Foster et al. |
| 2019/0359957 A1 | 11/2019 | Foster et al. |

FOREIGN PATENT DOCUMENTS

| | | | |
|---|---|---|---|
| CN | 106795537 A | 5/2017 | |
| CN | 107849300 A | 3/2018 | |
| EP | 995490 A2 | 4/2000 | |
| EP | 1728853 | 12/2006 | |
| EP | 1938892 A1 | 7/2008 | |
| EP | 3399015 | 11/2018 | |
| JP | S49124358 A | 11/1974 | |
| JP | H03127983 A | 5/1991 | |
| JP | 2007185133 A | 7/2007 | |
| JP | 2009225662 A | 10/2009 | |
| JP | 2013179909 A | 9/2013 | |
| RU | 2644344 C1 | 2/2018 | |
| WO | 2008094282 A1 | 8/2008 | |
| WO | 2010003007 A2 | 1/2010 | |
| WO | 2010069313 A1 | 6/2010 | |
| WO | 2013090769 | 6/2013 | |
| WO | 2013186340 A1 | 12/2013 | |
| WO | 2014093505 A2 | 6/2014 | |
| WO | 2014105793 A1 | 7/2014 | |
| WO | 2014105797 A2 | 7/2014 | |
| WO | WO-2015032375 A1 * | 3/2015 | ............ C12M 21/04 |
| WO | 2015117019 A1 | 8/2015 | |
| WO | 2015149147 A1 | 10/2015 | |
| WO | 2015195654 A1 | 12/2015 | |
| WO | 2017115855 | 7/2017 | |
| WO | 2017165244 A1 | 9/2017 | |
| WO | 2018005770 A2 | 1/2018 | |
| WO | 2018022595 A1 | 2/2018 | |
| WO | 2018022633 A1 | 2/2018 | |
| WO | 2018106549 A1 | 6/2018 | |
| WO | 2013152051 A2 | 10/2019 | |
| WO | 2019191761 A1 | 10/2019 | |
| WO | 2019191763 A1 | 10/2019 | |
| WO | 2019191767 A1 | 10/2019 | |
| WO | 2019191770 A1 | 10/2019 | |
| WO | 2019191772 A1 | 10/2019 | |
| WO | 2019213108 A1 | 11/2019 | |
| WO | 2019213118 A1 | 11/2019 | |

OTHER PUBLICATIONS

Hensirisak et al. "Scale-Up of Microbubble Dispersion Generator for Aerobic Fermentation", Applied Biochemistry and Biotechnology vol. 101, 2002, p. 211-227 (Year: 2002).*

Kaster et al., "Increased Oxygen Transfer in a Yeast Fermentation Using a Microbubble Dispersion", Applied Biochemistry and Biotechnology vol. 24/25, 1990, p. 469-484 (Year: 1990).*

Huang et al., "Bacterial and Yeast Cultures—Process Characteristics, Products, and Applications", Bioprocessing for Value-Added Products from Renewable Resources (pp. 185-223) Dec. 2007 (Year: 2007).*

Hensirisak et al., "Scale-Up of Microbubble Dispersion Generator for Aerobic Fermentation", Applied Biochemistry and Biotechnology, vol. 101, 2002, 211-227 (Year: 2002).*

Kirk et al., Quantification of the oxygen uptake rate in a dissolved oxygen controlled oscillating jet-driven microbioreactor, DOI 10.1002/jctb.4833, 2015 (Year: 2015).*

Ghosalkar et al., "Oxygen Uptake Rate Measurement by Modified Dynamic Method and Effect of Mass-Transfer Rates on Growth of Pichia Stipitis: Modeling and Experimental Data Comparison", Austin J Biotechnol Bioeng. 2016; 3(3): 1066 (Year: 2016).*

Lopes et al., "Over-Pressurized Bioreactors: Application to Microbial Cell Cultures", DOI 10.1002/btpr.1917 Published online May 8, 2014 in Wiley Online Library (wileyonlinelibrary.com) (Year: 2014).*

International Application No. PCT/US2019/025189, "International Search Report and Written Opinion", dated Jul. 2, 2019, 13 pages.

Abayomi, Oluwanbe Johnson., et al., "An engineered constitutive promoter set with broad activity range for Cupriavidus necator H16", Acs Synthetic Biology, vol. 7, (Jun. 27, 2018), XP002792846, Jun. 27, 2018, pp. 1918-1928.

Atlic, et al., "Continuous Production of Poly([R]-3-Hydroxybutyrate) by Cupriavidus Necator in a Multistage Bioreactor Cascade", Applied Microbialogy and Biotechnology, vol. 91, 2011, pp. 295-304.

Brigham, C.J., et al., "Engineering Ralstonia eutropha for Production of Isobutanol from CO2, H2 and O2", Advanced Biofuels and Bioproducts, (2013) Chapter 39, pp. 1065-1090.

Byrd, et al. "Bacterial Control of Agromyces Ramosus in Soil Canadian Journal of Microbiology", vol. 31, No. 12, 1985, pp. 1157-1163.

Chae, Tong Un., et al., Metabolic engineering of *Escherichia colifor* the production of four-, five- and six-carbon lactams Metabolic Engineering, Academic Press, Us, vol. 41 Apr. 5, 2017 82-91.

Chi, Nguyen, et al., "Trapping the dynamic acyl carrier protein in fatty acid biosynthesis", Nature, vol. 505, No. 7483, Dec. 22, 2013, pp. 427-431.

Eggers, et al., "Impact of Ralstonia Eutropha's Poly(3-Hydroxybutyrate) (PHB) Depolymerases and Phasins on PHB Storage in Recombinant *Escherichia coli*", Applied and Environmental Microbiology, vol. 80, No. 24, Dec. 2014, pp. 7702-7709.

Feng, Yanbin, et al., "Tuning of acyl-ACP thioesterase activity directed for tailored fatty acid synthesis Applied Microbiology And Biotechnology", Springer, De, vol. 102, No. 7, Feb. 22, 2018, pp. 3173-3182.

Fernando, Silva, et al., "Impact of nitrogen feeding regulation on polyhydroxyalkanoates production by mixed microbial cultures", New Biotechnology, vol. 37, XP029943712 2017, pp. 90-98.

Gabriela, Montiel-Jarillo, et al., "Enrichment of a mixed microbial culture for polyhydroxyalkanoates production: Effect of pH and N and P concentrations", Science Of The Total Environment, vol. 583, XP029914697, 2017, pp. 300-307.

Girdhar, Amandeep, et al., "Process Parameters for Influencing Polyhydroxyalkanoate Producing Bacterial Factories: An Overview", Journal of Petroleum & Environmental Biotechnology, vol. 4, No. 5, 2013, pp. 8.

Hanko, Erik K. R.., et al., "Characterisation of a 3-hydroxypropionic acid-inducible system from Pseudomonas putida for orthogonal gene expression control in *Escherichia coli* and Cupriavidus necator", Scientific Reports, vol. 7, XP002792878, 2017, pp. 1-12.

Horvat, et al., "Mathematical Modelling and Process Optimization of a Continuous 5-Stage Bioreactor Cascade for Production of Poly[-(R)-3-Hydroxybutyrate] by Cupriavidus Necator", Bioprocess Biosyst Eng, vol. 36, 2013, pp. 1235-1250.

Hun-Suk, Song, et al. "Enhanced isobutanol production from acetate by combinatorial overexpression of acetyl-CoA synthetase and anaplerotic enzymes in engineered *Escherichia coli*", Biotechnology And Bioengineering, vol. 115, (May 2, 2018), XP002792879, May 2, 2018, pp. 1971-1978.

International Application No. PCT/US2019/025194, "Invitation to Pay Additional Fees and, Where Applicable, Protest Fee", dated Jul. 1, 2019, 15 pages.

International Search Report and Written Opinion for International Application No. PCT/US2019/025202, dated Jul. 30, 2019, 13 pages.

Tanaka et al., "Production of Poly(D-3-Hydroxybutyrate) from CO2, H2, and O2 by High Cell Density Autotrophic7 Cultivation of Alcaligenes Eutrophus", Biotechnology and Bioengineering, vol. 45, No. 3, Feb. 5, 1995, pp. 268-275.

International Search Report and Written Opinion for International Application Serial No. PCT/US2019/025194, mailed on Aug. 22, 2019, pp. 8.

(56) References Cited

OTHER PUBLICATIONS

International Search Report and Written Opinion for International Application Serial No. PCT/US2019/025211, Mailed on Jul. 29, 2019, pp. 9.
International Search Report and Written Opinion for International Application Serial No. PCT/US2019/025218, mailed on Sep. 5, 2019, pp. 17.
International Search Report and Written Opinion for International Application Serial No. PCT/US2019/029956, mailed Aug. 13, 2019, pp. 6.
International Search Report and Written Opinion for International Application Serial No. PCT/US2019/029973, mailed on Jul. 23, 2019, pp. 5.
Ishizaki, A., et al., "Microbial production of poly-D-3-hydroxybutyrate from CO2", Applied Microbiology and Biotechnology, vol. 57, Oct. 2001, pp. 6-12.
Janina, Kluge, et al. "Inducible promoters and functional genomic approaches for the genetic engineering of filamentous fungi", Applied Microbiology And Biotechnology, vol. 102, (Jun. 1, 2018), XP036546152, Jun. 2, 2018, pp. 6357-6372.
Jayashree, Chakravarty, et al., "Solvent production by engineered Ralstonia eutropha: channeling carbon to biofuel", Applied Microbiology And Biotechnology, vol. 102, (Apr. 29, 2018), XP036507417, early online publication Apr. 29, 2018 5021-5031.
Jiachao, Zhu, et al., "Factors for promoting polyhydroxyalkanoate (PHA) synthesis in bio-nutrient-removal and recovery system" 4th International Conference on Environmental Systems Research (ICESR 2017) Conference paper, XP002792821, DOI: 10.1088/1755-1315/178/1/012021, cited as a P-document, but the conference was held in 2017, 2018, pp. 1-4.
Jillian, Marc, et al., "Over expression of GroESL in Cupriavidus necator for heterotrophic and autotrophic isopropanol production", Metabolic Engineering, vol. 42, XP085136193 2017, pp. 74-84.
Jones, G.W. and Kennedy, R.E., "Prevention of Gas Explosions by Controlling Oxygen Concentration", Industrial and Engineering Chemistry, vol. 27, Issue 11, 1935, pp. 1344-1346.
Joris, Beld, et al., Evolution of acyl-ACP thioesterases and [beta]-ketoacyl-ACP synthases revealed by protein-protein interactions Journal Of Applied Phycology., vol. 26, No. 4 Nov. 22, 2013 1619-1629.
Judger, B-E., et al., "An analysis of the changes in soluble hydrogenase and global gene expression in Cupriavidus necator (Ralstonia eutropha) HI6 grown in heterotrophic diauxic batch culture", Microbial Cell Factories, vol. 14, 2015, pp. 1-11.
Justyna, Mozejko-Ciesielska, et al., "Bacterial polyhydroxyalkanoates: Still fabulous?", Microbiological Research, vol. 192, XP029740446, and reference Horng 2016, pp. 271-282.
Katalin, Kovacs, et al. Metabolic engineering of Cupriavidus necator H16 for the sustainable production of C3 and C5 monomers and polymers CInet Conference 4, Conference paper (Abstract), 2019, XP002792880, The oral disclosure may have been more important (?); the publication date is presumably, Jan. 2019, 26 pgs.
Kianoush, Khosravi-Darani, et al., "Simulation of bioreactors for poly(3-hydroxybutyrate) production from natural gas Iranian Journal Of Chemistry And Chemical Engineering, vol. 39, XP002792822, (Modeling of . . . ); online publication in late 2018, pp. 1-24.
Klasson, K.T., et al.,"Bioreactor design for synthesis gas fermentations", Fuel , vol. 70, Issue 5, 1991, pp. 605-614.
Koller, et al., "Potential and Prospects of Continuous Polyhydroxyalkanoate (PHA)", Production Bioengineering, May 29, 2015, pp. 94-121.
Koller, M., "A review on established and emerging fermentation schemes for microbial production of polyhydroxyalkanoate (PHA) biopolyesters", Fermentation, vol. 4, (Apr. 23, 2018), XP002792757, early online publication Apr. 23, 2018, pp. 1-30.
Kunasundari, et al., "Revisiting the Single Cell Protein Application of Cupriavidus Necator H16 and Recovering Bioplastic Granules Simultaneously", Plos One, vol. 8, No. 10 Oct. 2013, 15 pgs.
Maddipati, P., "Ethanol production from syngas by Clostridium strain P11 using com steep liquor as a nutrient replacement to yeast extract", Bioresoure Technology, vol. 102, Issue 11, 2011, pp. 6494-6501.
Makkar, et al., "*Cupriavidus necator* Gen. Nov., Sp. Nov.: A Nonobligate Bacterial Predator of Bacteria in Soil", International Journal of Systematic Bacteriology, vol. 37, No. 4, Oct. 1987, pp. 323-326.
Marika, Zlesack, et al., "Chimeric Fatty Acyl-Acyl Carrier Protein Thioesterases Provide Mechanistic Insight into Enzyme Specificity and Expression", Applied And Environmental Microbiology, vol. 84, No. 10, Mar. 16, 2018, pp. 12.
Martin, Koller, et al., "Continuous production mode as a viable process-engineering tool for efficient poly (hydroxyalkanoate) (PHA) bio-production", Chemical And Biochemical Engineering Quarterly, vol. 28, XP002792820, 2014, pp. 65-77.
Matthias, Raberg, et al., "Ralstonia eutropha H16 in progress: applications beside PHAs and establishment as production platform by advanced genetic tools", Critical Reviews In Biotechnology, vol. 38, (Dec. 12, 2017), XP002792845, early online publication Dec. 12, 2017, pp. 494-510.
Miglena, Manandhar, et al., "Pimelic acid, the first precursor of the Bacillus subtilis biotin synthesis pathway, exists as the free acid and is assembled by fatty acid synthesis", Molecular Microbiology, vol. 104, No. 4, Mar. 3, 2017, pp. 595-607.
Phillips, J.R., et al., "Syngas Fermentation: A Microbial Conversion Process of Gaseous Substrates to Various Products", Fermentation, vol. 3, Issue 2, 2017, pp. 26.
Raberg, et al., "A Closer Look on the Polyhydroxybutyrate-(PHB-) Negative Phenotype of Ralstonia Eutropha PHB-4", Plos One, vol. 9, No. 5, May 2014, pp. 1-11.
Robert, Haushalter W., et al., "Production of Odd-Carbon Dicarboxylic Acids in *Escherichia coli* Using an Engineered Biotin-Fatty Acid Biosynthetic Pathway", Journal Of The American Chemical Society, vol. 139, No. 13, Mar. 21, 2017, pp. 4615-4618.
Russell, J.B., "The Energy Spilling Reactions of Bacteria and Other Organisms", Journal of Molecular Microbiology Biotechnology, vol. 13, No. 1, 2007, pp. 1-11.
Shively, J.M. et al., "Something From Almost Nothing: Carbon Dioxide Fixation in Chemoautotrophs", Annual Review of Microbiology, vol. 52, 1998, pp. 191-230.
Sillman, et al., Isolation of Nonobligate Bacterial Predators of Bacteria from Soil Canadian Journal of Microbiology, vol. 32, No. 9, 1986, pp. 760-762.
Swathi, Alagesan, et al., "Functional genetic elements for controlling gene expression in Cupriavidus necator H16", Applied And Environmental Microbiology, vol. 84, (Oct. 2018), XP055604488, Oct. 2018, pp. 1-17.
Tanaka, K. and Ishizaki, A., "Production of poly-d-3-hydroxybutyric acid from carbon dioxide by a two-stage culture method employing Alcaligenes eutrophus ATCC 17697T", Journal of Fermentation and Bioengineering, vol. 77, Issue 4, 1994, pp. 425-427.
Zeph, et al., "Gram-Negative Versus Gram-Positive (Actinomycete) Nonobligate Bacterial Predators of Bacteria in Soil", Applied Environmental Microbiology, vol. 52, No. Oct. 4, 1986, pp. 819-823.
NETL brochure, "Syngas composition", accessed online at https://www.netl.doe.gov/research/coal/energy-systems/gasification/gasifipedia/syngas-composition, Jul. 3, 2021, pp. 2. (Year: 2021).
"Aminotransferase class III-fold pyridoxal phosphate-dependent enzyme [Aquitalea denitrificans]", NCBI Reference Sequence: WP_159877958.1, Jan. 19, 2020, 1 page.
"Aminotransferase class III-fold pyridoxal phosphate-dependent enzyme [*Aquitalea* sp. LB_tupeE]", NCBI Reference Sequence: WP_178973970.1, Jul. 11, 2020, 1 page.
"Aminotransferase class III-fold pyridoxal phosphate-dependent enzyme [Chromobacterium haemolyticum]", NCBI Reference Sequence: WP_166453011.1, Apr. 6, 2020, 1 page.
"Aminotransferase class III-fold pyridoxal phosphate-dependent enzyme [Chromobacterium vaccinii]", NCBI Reference Sequence: WP_166440807.1, Apr. 6, 2020, 1 page.

(56) References Cited

OTHER PUBLICATIONS

"Aminotransferase class III-fold pyridoxal phosphate-dependent enzyme [Crenobacter sedimenti]", NCBI Reference Sequence: WP_163315775.1, Apr. 6, 2020, 1 page.
"Aminotransferase class III-fold pyridoxal phosphate-dependent enzyme [Neisseriaceae bacterium B2N2-7]", GenBank: MXR37125.1, Jan. 6, 2020, 2 pages.
"Aminotransferase class III-fold pyridoxal phosphate-dependent enzyme [Paludibacterium paludis]", NCBI Reference Sequence: WP_189532963.1, Sep. 28, 2020, 1 page.
"Aminotransferase class III-fold pyridoxal phosphate-dependent enzyme [*Paludibacterium* sp. dN 18-1]", GenBank: MTD33855.1, Nov. 24, 2019, 1 page.
"Aminotransferase class III-fold pyridoxal phosphate-dependent enzyme [Vogesella alkaliphila]", NCBI Reference Sequence: WP_189374996.1, Sep. 28, 2020, 1 page.
"Aminotransferase class III-fold pyridoxal phosphate-dependent enzyme [Vogesella fluminis]", NCBI Reference Sequence: WP_189352298.1, Sep. 28, 2020, 1 page.
"Aminotransferase class III-fold pyridoxal phosphate-dependent enzyme [Vogesella oryzae]", NCBI Reference Sequence: WP_174874069.1, Jun. 22, 2020, 1 page.
"Aspartate aminotransferase family protein [Aquitalea magnusonii]", NCBI Reference Sequence: WP_059287319.1, Dec. 31, 2020. 1 page.
"Aspartate aminotransferase family protein [Aquitalea magnusonii]", NCBI Reference Sequence: WP_089085350.1, Jul. 15, 2017, 1 page.
"Aspartate aminotransferase family protein [*Aquitalea* sp. FJL05]", NCBI Reference Sequence: WP_124643387.1, Apr. 12, 2019, 1 page.
"Aspartate aminotransferase family protein [*Aquitalea* sp. THG-DN7.12]", NCBI Reference Sequence: WP_137009623.1, Oct. 16, 2019, 1 page.
"Aspartate aminotransferase family protein [Chromobacterium amazonense]", NCBI Reference Sequence: WP_106076402.1, Mar. 16, 2018, 1 page.
"Aspartate aminotransferase family protein [Chromobacterium haemolyticum]", GenBank: OQS32233.1, Apr. 6, 2017, 2 pages.
"Aspartate aminotransferase family protein [Chromobacterium haemolyticum]", GenBank: OQS37730.1, Apr. 6, 2017, 2 pages.
"Aspartate aminotransferase family protein [Chromobacterium haemolyticum]", NCBI Reference Sequence: WP_043593957.1, Apr. 15, 2016, 1 page.
"Aspartate aminotransferase family protein [Chromobacterium haemolyticum]", NCBI Reference Sequence: WP_081556739.1, Apr. 8, 2017, 1 page.
"Aspartate aminotransferase family protein [Chromobacterium haemolyticum]", NCBI Reference Sequence: WP_081576047.1, Apr. 8, 2017, 1 page.
"Aspartate aminotransferase family protein [Chromobacterium haemolyticum]", NCBI Reference Sequence: WP_161523523.1, Oct. 5, 2020, 1 page.
"Aspartate aminotransferase family protein [Chromobacterium paludis]", NCBI Reference Sequence: WP_149295777.1, Oct. 5, 2020, 1 page.
"Aspartate aminotransferase family protein [Chromobacterium phragmitis]", NCBI Reference Sequence: WP_114062556.1, Dec. 20, 2020.
"Aspartate aminotransferase family protein [*Chromobacterium* sp. ATCC 53434]", NCBI Reference Sequence: WP_101708025.1, Jan. 10, 2018.
"Aspartate aminotransferase family protein [*Chromobacterium* sp. LK11]", NCBI Reference Sequence: WP_048412320.1, Apr. 15, 2016, 1 page.
"aspartate aminotransferase family protein [*Chromobacterium* sp. LK1]", NCBI Reference Sequence: WP_048411976.1, Apr. 15, 2016, 1 page.
"Aspartate aminotransferase family protein [*Chromobacterium* sp. MWU13-2610]", NCBI Reference Sequence: WP_103321487.1, Jan. 31, 2018, 1 page.
"Aspartate aminotransferase family protein [*Chromobacterium* sp. MWU14-2602]", NCBI Reference Sequence: WP_103903523.1, Feb. 10, 2018, 1 page.
"Aspartate aminotransferase family protein [*Chromobacterium* sp. *panama*]", NCBI Reference Sequence: WP_107799474.1, Apr. 25, 2018, 1 page.
"Aspartate aminotransferase family protein [Chromobacterium sphagni]", NCBI Reference Sequence: WP_071116856.1, Aug. 23, 2017, 1 page.
"Aspartate aminotransferase family protein [Chromobacterium subtsugae]", NCBI Reference Sequence: WP_047237256.1, Mar. 20, 2018, 1 page.
"Aspartate aminotransferase family protein [Chromobacterium subtsugae]", NCBI Reference Sequence: WP_047243213.1, Apr. 15, 2016, 1 page.
"Aspartate aminotransferase family protein [Chromobacterium subtsugae]", NCBI Reference Sequence: WP_047257673.1, Apr. 15, 2016, 1 page.
"Aspartate aminotransferase family protein [Chromobacterium vaccinii]", NCBI Reference Sequence: WP_046156378.1, Oct. 25, 2019, 1 page.
"Aspartate aminotransferase family protein [Chromobacterium vaccinii]", NCBI Reference Sequence: WP_104946997.1, Mar. 4, 2018, 1 page.
"Aspartate aminotransferase family protein [Chromobacterium violaceum]", NCBI Reference Sequence: WP_011135573.1, Jul. 28, 2019, 1 page.
"Aspartate aminotransferase family protein [Chromobacterium violaceum]", NCBI Reference Sequence: WP_048405256.1, Apr. 15, 2016, 1 page.
"Aspartate aminotransferase family protein [Chromobacterium violaceum]", NCBI Reference Sequence: WP_081573061.1, Apr. 8, 2017, 1 page.
"Aspartate aminotransferase family protein [Chromobacterium violaceum]", NCBI Reference Sequence: WP_152637556.1, Oct. 31, 2019, 1 page.
"Aspartate aminotransferase family protein [*Crenobacter* sp. GY 70310]", NCBI Reference Sequence: WP_136552942.1, Oct. 16, 2019, 1 page.
"Aspartate aminotransferase family protein [Gulbenkiania indica]", NCBI Reference Sequence: WP_055434103.1, May 14, 2017, 1 page.
"Aspartate aminotransferase family protein [Gulbenkiania mobilis]", NCBI Reference Sequence: WP_054286466.1, May 14, 2017, 1 page.
"Aspartate aminotransferase family protein [Paludibacterium purpuratum]", NCBI Reference Sequence: WP_133682408.1, May 12, 2019, 1 page.
"Aspartate aminotransferase family protein [Paludibacterium yongneupense]", NCBI Reference Sequence: WP_028535161.1, Apr. 15, 2016, 2 pages.
"Aspartate aminotransferase family protein [Pseudogulbenkiania ferrooxidans]", NCBI Reference Sequence: WP_008952788.1, Apr. 15, 2016, 2 pages.
"Aspartate aminotransferase family protein [Pseudogulbenkiania ferrooxidans]", NCBI Reference Sequence: WP_021478068.1, Apr. 15, 2016, 1 page.
"Aspartate aminotransferase family protein [*Pseudogulbenkiania* sp. MAI-1]", NCBI Reference Sequence: WP_024302818.1, Apr. 15, 2016, 2 pages.
"Aspartate aminotransferase family protein [*Pseudogulbenkiania* sp. NH8B]", NCBI Reference Sequence: WP_014087389.1, Apr. 15, 2016, 2 pages.
"Aspartate aminotransferase family protein [Pseudogulbenkiania subflava]", NCBI Reference Sequence: WP_085275708.1, Apr. 22, 2017, 1 page.
"Aspartate aminotransferase family protein [Vogesella indigofera]", NCBI Reference Sequence: WP_120809711.1, Nov. 4, 2018, 1 page.
"Aspartate aminotransferase family protein [Vogesella mureinivorans]", NCBI Reference Sequence: WP_147694092.1, Oct. 5, 2020, 1 page.
"Aspartate aminotransferase family protein [Vogesella perlucida]", NCBI Reference Sequence: WP_147687830.1, Oct. 5, 2020, 1 page.

(56) References Cited

OTHER PUBLICATIONS

"aspartate aminotransferase family protein [*Vogesella* sp. EB]", NCBI Reference Sequence: WP_047966302.1, Apr. 15, 2016, 1 page.
"Aspartate aminotransferase family protein [*Vogesella* sp. LIG4]", NCBI Reference Sequence: WP_088967522.1, Jul. 11, 2017, 1 page.
"Aspartate aminotransferase family protein [Vogesella urethralis]", NCBI Reference Sequence: WP_144371715.1, Oct. 5, 2020, 1 page.
"Aspartate aminotransferase family protein [*Xenophilus* sp. AP218F]", NCBI Reference Sequence: WP_088737038.1, Jul. 3, 2017, 1 page.
"Crystal structure of the omega transaminase from Chromobacterium violaceum in complex with PMP", PDB: 6S4G_A, Dec. 1, 2020, 2 pages.
"Cupriavidus necator", Wikipedia, Retrieved from Internet URL: https://en.wikipedia.org/wiki/Cupriavidus_necator#:~:text=Cupriavidus%20necator%20is%20a%20hydrogen,a%20source%20of%20energy%20C., Feb. 25, 2021, 7 Pages.
"Multispecies: aspartate aminotransferase family protein [Aquitalea]", NCBI Reference Sequence: WP_045848621.1, Apr. 15, 2016, 1 page.
"Multispecies: aspartate aminotransferase family protein [Aquitalea]", NCBI Reference Sequence: WP_103523625.1, Agust 06, 2020, 1 page.
"Multispecies: aspartate aminotransferase family protein [Chromobacterium]", NCBI Reference Sequence: WP_019104435.1, Apr. 18, 2017, 1 page.
"Multispecies: aspartate aminotransferase family protein [Chromobacterium]", NCBI Reference Sequence: WP_043572477.1, Apr. 15, 2016, 1 page.
"Multispecies: aspartate aminotransferase family protein [Chromobacterium]", NCBI Reference Sequence: WP_043629242.1, Oct. 31, 2016, 1 page.
"Multispecies: aspartate aminotransferase family protein [Chromobacterium]", WP_043638691.1, Nov. 11, 2020, 1 page.
"Multispecies: aspartate aminotransferase family protein [Microvirgula]", NCBI Reference Sequence: WP_028498438.1, Jul. 14, 2018, 1 page.
"TPA: aspartate aminotransferase family protein [Betaproteobacteria bacterium]", GenBank: HEL32111.1, Mar. 2, 2020, 1 page.
Alagesan, S, et al., "13C-assisted metabolic flux analysis to investigate heterotrophic and mixotrophic metabolism in Cupriavidus necator H16", Metabolomics, vol. 14, Issue 9, 2018, 9 pgs.
Anderson, A. J.., et al., "Occurrence, Metabolism, Metabolic Role, and Industrial Uses of Bacterial Polyhydroxyalkanoates", Microbiological Review, 54(4), 1990, pp. 450-472.
U.S. Appl. No. 16/372,072, Corrected Notice of Allowability mailed Jan. 26, 2021, 2 pages.
U.S. Appl. No. 16/372,072, Non Final Office Action mailed Mar. 6, 2020, 20 pages.
U.S. Appl. No. 16/372,072, Notice of Allowance mailed Jul. 17, 2020, 11 pages.
U.S. Appl. No. 16/372,072, Notice of Allowance mailed Dec. 16, 2020, 9 pages.
U.S. Appl. No. 16/372,072, Preliminary Amendment filed Jul. 30, 2019, 5 pages.
U.S. Appl. No. 16/372,072, Preliminary Amendment filed Aug. 14, 2019, 5 pages.
U.S. Appl. No. 16/372,072, Response filed Feb. 11, 2020 to Restriction Requirement mailed Dec. 11, 2019, 7 pages.
U.S. Appl. No. 16/372,072, Response filed Jun. 8, 2020 to Non Final Office Action mailed Mar. 6, 2020, 11 pages.
U.S. Appl. No. 16/372,072, Restriction Requirement mailed Dec. 11, 2019, 9 pages.
U.S. Appl. No. 16/372,083, Non Final Office Action mailed Apr. 27, 2021, 14 pages.
U.S. Appl. No. 16/372,083, Notice of Allowance mailed Aug. 31, 2021, 9 pages.
U.S. Appl. No. 16/372,083, Preliminary Amendment filed Jul. 30, 2019, 143 pages.
U.S. Appl. No. 16/372,083, Response filed Apr. 12, 2021 to Restriction Requirement mailed Mar. 8, 2021, 8 pages.
U.S. Appl. No. 16/372,083, Response filed Jul. 27, 2021 to Non Final Office Action mailed Apr. 27, 2021, 11 pages.
U.S. Appl. No. 16/372,083, Response filed Dec. 18, 2020 to Restriction Requirement mailed Oct. 19, 2020, 7 pages.
U.S. Appl. No. 16/372,083, Restriction Requirement mailed Mar. 8, 2021, 6 pages.
U.S. Appl. No. 16/372,083, Restriction Requirement mailed Oct. 19, 2020, 8 pages.
U.S. Appl. No. 16/372,083, Supplemental Amendment filed for Non-Final Office Action mailed Apr. 27, 2021, 8 pages.
U.S. Appl. No. 16/372,099, Non Final Office Action mailed Jul. 9, 2021, 14 pages.
U.S. Appl. No. 16/372,099, Response filed May 18, 2021 to Restriction Requirement mailed Mar. 19, 2021, 7 pages.
U.S. Appl. No. 16/372,099, Restriction Requirement mailed Mar. 19, 2021, 6 Pages.
U.S. Appl. No. 16/372,106, Non Final Office Action mailed Apr. 30, 2021, 26 pages.
U.S. Appl. No. 16/372,106, Response filed Jan. 19, 2021 to Restriction Requirement mailed Dec. 28, 2020, 8 pages.
U.S. Appl. No. 16/372,106, Response filed Jun. 15, 2021 to Non Final Office Action mailed Apr. 30, 2021, 12 pages.
U.S. Appl. No. 16/372,106, Restriction Requirement mailed Dec. 28, 2020, 7 pages.
U.S. Appl. No. 16/398,384, Non Final Office Action mailed Oct. 23, 2020, 13 pages.
U.S. Appl. No. 16/399,145, Advisory Action mailed Feb. 1, 2021, 4 pages.
U.S. Appl. No. 16/399,145, Final Office Action mailed Dec. 4, 2020, 17 pages.
U.S. Appl. No. 16/399,145, Non Final Office Action mailed Jun. 17, 2021, 20 pages.
U.S. Appl. No. 16/399,145, Non Final Office Action mailed Aug. 12, 2020, 16 pages.
U.S. Appl. No. 16/399,145, Response filed Jan. 25, 2021 to Final Office Action mailed Dec. 4, 2020, 12 pages.
U.S. Appl. No. 16/399,145, Response filed Jun. 3, 2020 to Restriction Requirement mailed Apr. 17, 2020, 7 pages.
U.S. Appl. No. 16/399,145, Response filed Sep. 15, 2021 to Non Final Office Action mailed Jun. 17, 2021, 11 Pages.
U.S. Appl. No. 16/399,145, Response filed Nov. 6, 2020 to Non Final Office Action mailed Aug. 12, 2020, 12 pages.
U.S. Appl. No. 16/399,145, Restriction Requirement mailed Apr. 17, 2020, 9 pages.
U.S. Appl. No. 16/399,155, Advisory Action mailed Jun. 1, 2020, 3 pages.
U.S. Appl. No. 16/399,155, Final Office Action mailed Mar. 5, 2020, 23 pages.
U.S. Appl. No. 16/399,155, Final Office Action mailed Jul. 28, 2021, 14 pages.
U.S. Appl. No. 16/399,155, Non Final Office Action mailed Feb. 16, 2021, 17 pages.
U.S. Appl. No. 16/399,155, Response filed May 5, 2020 to Final Office Action mailed Mar. 5, 2020, 12 pages.
U.S. Appl. No. 16/399,155, Response filed May 14, 2021 to Non Final Office Action mailed Feb. 16, 2021, 11 pages.
U.S. Appl. No. 16/399,155, Response filed Jun. 5, 2020 to Advisory Action mailed Jun. 1, 2020, 13 pages.
U.S. Appl. No. 16/399,155, Response filed Jun. 5, 2020 to Final Office Action mailed Mar. 5, 2020, 13 pages.
Bramer, C O., "The malate dehydrogenase of Ralstonia eutropha and functionality of the C(3)/C(4) metabolism in a Tn5-induced mdh mutant", FEMS Microbiol Letters, vol. 212, Issue 2, Jul. 2, 2002, pp. 159-164.
Brandt, U, et al., "Elevated poly(3-hydroxybutyrate) synthesis in mutants of Ralstonia eutropha H16 defective in ipopolysaccharide biosynthesis", Applied Microbiology and Biotechnology, 2012, vol. 95, 2012, pp. 471-483.
Brigham, C J., et al., "Correction for Whole-genome microarray and gene deletion studies reveal regulation of the polyhydroxyalkanoate

(56) References Cited

OTHER PUBLICATIONS production cycle by the stringent response in Ralstonia eutropha H16", Appl Environ Microbiol., vol. 83, Issue 15, 2017, pp. 1-2.
Brigham, C J., et al., "Whole-genome microarray and gene deletion studies reveal regulation of the polyhydroxyalkanoate production cycle by the stringent response in Ralstonia eutropha H16", Appl Environ Microbiol., vol. 78, Issue 22, 2012, pp. 8033-8044.
Brown, D R., et al., "Nitrogen stress response and stringent response are coupled in *Escherichia coli*", Nature communications, 2014, vol. 5, 4115, , 8 pgs.
Bruland, et al., "Unravelling the C3/C4 carbon metabolism in Ralstonia eutropha H16", Journal of Applied Microbiology, 109, 2010, pp. 79-90.
Chen, R, et al., "A highly active decarboxylating dehydrogenase with rationally inverted coenzyme specificity", PNAS, vol. 92, Issue 25, 1996, pp. 11666-11670.
Chen, R, et al., "Redesigning secondary structure to invert coenzyme specificity in isopropylmalate dehydrogenase", PNAS, vol. 93, 1996, pp. 12171-12176.
Choi, J C., et al., "Modulation of 3-hydroxyvalerate molar fraction in poly(3-hydroxybutyrate-3-hydroxyvalerate) using Ralstonia eutropha transformant co-amplifying phbC and NADPH generation-related zwf genes", Enzyme and Microbiol Technology, vol. 32, Issue 1, 2003, pp. 178-185 (Abstract Only).
Cramm, R. J., "Genomic view of energy metabolism in Ralstonia eutropha HI6", Journal of Molecular Microbiology and Biotechnology, vol. 16, 2009, pp. 38-52.
Deveraux, J., et al., "A comprehensive set of sequence analysis programs for the VAX", Nucleic Acids Research, 12 (1 Part 1), 1984, pp. 387-395.
Devos, et al., "Practical limits of function prediction", Proteins: Structure, Function, and Genetics vol. 41, 2000, pp. 98-107.
Ding, H, et al., "Glycerol utilization by Rhizobium leguminosarum requires an ABC transporter and affects competition for nodulation", Microbiology, vol. 158, 2012, pp. 1369-1378.
Doberstein, C., et al., "Polythioester synthesis in Ralstonia eutropha H16: novel insights into 3,3'-thiodipropionic acid and 3,3'-dithiodipropionic acid catabolism", Journal of Biotechnology, vol. 184, 2014, pp. 187-198 (Abstract Only).
Du, et al., "Effects of Environmental Conditions on Cell Growth and Poly-β-Hydroxybutyrate Accumulation in Alcaligenes Eutrophus", World Journal of Microbiology & Biotechnology, vol. 16, 2000, pp. 9-13.
Gao, C, et al., "Lactate utilization is regulated by the FadR-type regulator LidR in Pseudomonas aeruginosa", Journal of Bacteriology, vol. 194, 2012, pp. 2687-2692.
Grousseau, et al., "Isopropanol Production with Engineered Cupriavidus Necator as Bioproduction Platform", Appl. Microbiol. Biotechnol., vol. 98, No. 9, 2014, pp. 4277-4290.
Gyaneshwar, et al., "Sulfur and Nitrogen Limitation in *Escherichia coli* K-12: Specific Homeostatic Responses", Journal of Bacteriology, vol. 187, No. 3, Feb. 2005, pp. 1074-1090.
Jauryliuk, V, et al., "Recent functional insights into the role of (p)ppGpp in bacterial physiology", Nature Reviews Microbiology, vol. 13, 2015, pp. 298-309.
Inoue, H, et al., "Biochemical and molecular characterization of the NAD(+)-dependent isocitrate dehydrogenase from the chemolithotrophAcidithiobacillus thiooxidans", FEMS Microbiol Letters, vol. 214, Issue 1, 2002, pp. 127-132.
International Application Serial No. PCT/US2019/025189, International Preliminary Report on Patentability mailed Oct. 15, 2020, 9 pages.
International Application Serial No. PCT/US2019/025194, International Preliminary Report on Patentability mailed Oct. 15, 2020, 15 pages.
International Application Serial No. PCT/US2019/025202, International Preliminary Report on Patentability mailed Oct. 15, 2020, 12 pages.
International Application Serial No. PCT/US2019/025218, Invitation to Pay Additional Fees mailed Jun. 25, 2019, 8 pages.
International Application Serial No. PCT/US2019/029795, International Preliminary Report on Patentability mailed Nov. 3, 2020, 8 pages.
International Application Serial No. PCT/US2019/029795, International Search Report mailed Jul. 11, 2019, 4 pages.
International Application Serial No. PCT/US2019/029795, Written Opinion mailed Jul. 11, 2019, 6 pages.
International Application Serial No. PCT/US2019/029798, International Preliminary Report on Patentability mailed Nov. 3, 2020, 14 pages.
International Application Serial No. PCT/US2019/029798, International Search Report mailed Sep. 12, 2019, 7 pages.
International Application Serial No. PCT/US2019/029798, Invitation to Pay Additional Fees mailed Jul. 22, 2019, 16 pages.
International Application Serial No. PCT/US2019/029798, Written Opinion mailed Sep. 12, 2019, 12 pages.
International Application Serial No. PCT/US2019/029817, International Preliminary Report on Patentability mailed Nov. 3, 2020, 14 pages.
International Application Serial No. PCT/US2019/029817, International Search Report mailed Sep. 23, 2019, 8 pages.
International Application Serial No. PCT/US2019/029817, Invitation to Pay Additional Fees mailed Aug. 1, 2019, 15 Pages.
International Application Serial No. PCT/US2019/029817, Written Opinion mailed Sep. 23, 2019, 12 pages.
International Application Serial No. PCT/US2019/029827, International Preliminary Report on Patentability mailed Nov. 3, 2020, 14 pages.
International Application Serial No. PCT/US2019/029827, International Search Report mailed Sep. 23, 2019, 9 pages.
International Application Serial No. PCT/US2019/029827, Invitation to Pay Additional Fees mailed Jul. 23, 2019, 17 Pages.
International Application Serial No. PCT/US2019/029827, Written Opinion mailed Sep. 23, 2019, 12 Pages.
International Application Serial No. PCT/US2019/029956, International Preliminary Report on Patentability mailed Nov. 12, 2020, 12 pages.
International Application Serial No. PCT/US2019/029973, International Preliminary Report on Patentability mailed Nov. 12, 2020, 12 pages.
International Preliminary Report on Patentability for PCT application No. PCT/US2019/025211, mailed on Oct. 15, 2020, 13 pages.
Ishii, et al., "Uniprot database", accession No. G2J4X6, 2011, 2 pages.
Shizuka, H, et al., "Putrescine Oxidase of Micrococcus Rubens: Primary Structure and *Escherichia coli*", Journal of General Microbiology, vol. 139, 1993, pp. 425-432.
Juengert, J. R., et al., "Absence of ppGpp Leads to Increased Mobilization of Intermediately Accumulated Poly(3-Hydroxybutyrate) in Ralstonia eutropha H16", Applied and Environmental Microbiology, vol. 83, Issue 13, 2017, pp. e00755-17 (1-16).
Kaddor, C, et al., "Effects of homologous phosphoenolpyruvate-carbohydrate phosphotransferase system proteins on carbohydrate uptake and poly(3-hydroxybutyrate) accumulation in Ralstonia eutropha H16", Appl. Environ. Microbiol. vol. 77, 2011, pp. 3582-3590.
Kaddor, C, et al., "Implications of various phosphoenolpyruvate-carbohydrate phosphotransferase system mutations on glycerol utilization and poly(3-hydroxybutyrate) accumulation in Ralstonia eutropha H16", AMB Express, vol. 1, 2011, pp. 16.
Karstens, K, et al., "Phosphotransferase protein EIIANtr interacts with SpoT, a key enzyme of the stringent response, in Ralstonia eutropha HI6", Microbiology, vol. 160, 2014, pp. 711-722.
Kazakov, A E., et al., "Comparative genomics of regulation of fatty acid and branched-chain amino acid utilization in proteobacteria", Journal of Bacteriology, vol. 191, 2009, pp. 52-64.
Kim, et al., "Effect of overexpression of Actinobacillus succinogenes phosphoenolpyruvate carboxykinase on succinate production in *Escherichia coli*", Appl Environ Microbiol., 70(2), Feb. 2004, pp. 1238-1241.
Kisselev, L, "Polypeptide Release Factors in Prokaryotes and Eukaryotes: Same Function, Different Structure", Structure vol. 10, 2002, pp. 8-9.

(56) References Cited

OTHER PUBLICATIONS

Kizer, et al., "Application of functional genomics to pathway optimization for increased isoprenoid production", Appl Environ Microbiol., 74(10) doi: 10.1128/AEM.02750-07. Epub Mar. 14, 2008, May 2008, pp. 3229-3241.

Krausse, et al., "Essential role of the hprK gene in Ralstonia eutropha HI6", J Mol Microbiol Biotechnol, vol. 17, 2009, pp. 146-152.

Kyte, Jack, et al., "A Simple Method for Displaying the Hydropathic Charcter of a Protein", Journal of Molecular Biology, 157, 1982, pp. 105-132.

Lardi, M, et al., "σ-54-Dependent Response to Nitrogen Limitation and Virulence in Burkholderia cenocepacia Strain H111", Appl. Environ. Microbiol., vol. 81, Issue 12, 2015, pp. 4077-4089.

Lee, et al., "Microbial Production of Ethanol from Acetate by Engineered Ralstonia Eutropha", Biotechnology and Bioprocess Engineering, vol. 21, 2016, pp. 402-407.

Lee, et al., "Regulation of poly-β-hydroxybutyrate biosynthesis by nicotinamide nucleotide in Alcaligene eutrophus", FEMS Microbiological letters, vol. 131, 1995, pp. 35-39.

Lee, J N., et al., "Metabolic Engineering of Pentose Phosphate Pathway in Ralsonia eutropha for Enhanced Biosynthesis of poly-β-hydroxybutyrate", Biotechnology Progress, vol. 19, Issue 5, 2003, pp. 1444-1449.

Lenczak, J. L., et al., "High cell density strategy for poly(3-hydroxybutyrate) production by Cupriavidus necator", Brazilian Journal of Chemical Engineering, vol. 28, Issue 4, 2011, pp. 585-596.

Leyn, et al., "Control of proteobacterial centralcarbon metabolism by the HexR transcriptionalregulator: a case study in Shewanella oneidensis", Journal of Biological Chemistry, vol. 286, Issue 41, 2011, pp. 35782-35794.

Leyn, S A., et al., "Comparative genomics and evolution of transcriptional regulons in Proteobacteria", Microbial Genomics, 2016, pp. 1-15.

Li, Z J., et al., "Overexpression of NAD kinase in recombinant *Escherichia coli* harboring the phbCAB operon improves poly(3-hydroxybutyrate) production", Appl Microbiol Biotechnol., vol. 83, Issue 5, 2009, pp. 939-947.

Lin, S, et al., "Biotin Synthesis Begins by Hijacking the Fatty Acid Synthesis Pathway", Nature Chemical Biology, vol. 6, No. 9, Sep. 2010, pp. 682-688.

Liu, X, "Comparative analysis of genes frequently regulated by drugs based on connectivity map transcriptome data", PLoS One, vol. 12, Issue 6, 2017, pp. e0179037 (1-13).

Lu, et al., "Studies in the production of branched-chain alcohols in engineered Ralstonia eutropha", Bioenergy and Biofuels, 96, 2012, 283-297.

Lu, et al., "Studies on the Production of Branched-chain Alcohols in Engineered Ralstonia Eutropha", Appl, Microbiol, Biotechnol, vol. 96, No. 1, 2012, 15 pgs.

Lucas, et al., "Gen Bank accession No. ACU95033", Aug. 26, 2009, p. 1.

March, J C., et al., "Expression of an anaplerotic enzyme, pyruvate carboxylase, improves recombinant protein production in *Escherichia coli*", Applied and Environmental Microbiology, vol. 68, Issue 11, 2002, pp. 5620-5624.

McKinlay, J. B., et al., "Carbon dioxide fixation as a central redox cofactor recycling mechanism in bacteria", PNAS, vol. 107, Issue 26, 2010, pp. 11669-11675.

Meng, J, et al., "High-yield anaerobic succinate production by strategically regulating multiple metabolic pathways based on stoichiometric maximumin *Escherichia coli*", Microbiol Cell Factories, vol. 15, 2016, 13 pgs.

Myers, Eugene, et al., "Optimal alignments in linear space", Computer Applications in the Biosciences, vol. 4, 1988, pp. 11-17.

Needleman, Saul, et al., "A general method applicable to the search for similarities in amino acid sequence of two proteins", Journal of Molecular Biology, vol. 48, Issue 3, 1970, pp. 443-453.

Non-final office action received for U.S. Appl. No. 16/398,351, mailed on Feb. 1, 2021, 24 pages.

Non-final office action received for U.S. Appl. No. 16/398,401, mailed on Feb. 16, 2021, 29 pages.

Non-final Office Action received for U.S. Appl. No. 16/398,365, mailed on Jan. 25, 2021, 10 Pages.

Obruca, S, et al., "Application of random mutagenesis to enhance the production of polyhydroxyalkanoates by Cupriavidus necator H16 on waste frying oil", World J Microbiol Biotechnol, 2013, vol. 29, 2013, pp. 2417-2428.

Olaya-Abril, et al., "Poly(3-hydroxybutyrate) hyperproduction by a global nitrogen regulator NtrB mutant strain of Paracoccus denitrificans PD1222", FEMS Microbiology Letters, vol. 365:fnx251, 2008, 8 pgs.

Orita, L, et al., "Identification of mutation points in Cupriavidus necator NCIMB 11599 and genetic reconstitution of Glucose-utilization ability in wild strain H16 for polyhydroxyalkanoate production", Journal of Bioscience and Bioengineering, vol. 113, Issue 1, 2012, pp. 63-69.

Papagiani, M, "Recent advances in engineering the central carbon metabolism of industrially important bacteria", Microbial Cell Factories, vol. 11, 2012, 13 pgs.

Park, J S., et al., "Metabolic Characteristics of Isocitrate Dehydrogenase Leaky Mutant of Alcaligene eutrophus and its Utilization for Poly-Hydroxybutyrate Production", Journal of Fermentation and Bioengineering, 1996, vol. 81, Issue 3, 1996, pp. 197-205.

Park, S, et al., "Oxaloacetate and malate production in engineered *Escherichia coli* by expression of codon-optimized phosphoenolpyruvate carboxylase2 gene from Dunaliella salina", Bioprocess Biosyst Eng., vol. 36 Issue 1, 2013, pp. 127-131 (Abstract Only).

Pearson, William R., et al., "Improved tools for biological sequence comparison", Proc Natl Acad Sci U S A, 85(8). 1988, pp. 2444-2448.

Persuhn, D C., et al., "The transcriptional activator NtrC controls the expression and activity of glutamine synthetase in Herbaspirillum seropedicae", FEMS Microbiology Letters, vol. 192, 2000, pp. 217-221.

Pohlmann, A, et al., "Genome sequence of the bioplastic-producing "Knallgas" bacterium Ralsonia eutropha H16", Nature Biotechnology, vol. 24, No. 10, 2007, pp. 1257-1262.

Prather KLJ et al. De nova biosynthetic pathways: Rational design of microbial chemical factories. Current Opinion in Biotechnology, 2008. 19:468-47 4 (Year: 2008).

Przybylski, et al., "Synthesis of the Building Block 2-Hydroxyisobutyrate from Fructose and Butyrate by Cupriavidus Necator H16", Appl, Microbiol, Biotechnol, vol. 97, 2013, pp. 8875-8885.

Qi, et al., "Model-driven redox pathway manipulation for improved isobutanol production in Bacillus subtilis complemented with experimental validation and metabolic profiling analysis", PLoS ONE, vol. 9, Issue 4, e93815, 2014, pp. 1-11.

Raberg, M, "Ralstonia eutropha H16 in progress: applications beside PHAs and establishment as production platform by advanced genetic tools", Critical Reviews in Biotechnology, vol. 38, Dec. 12, 2017, pp. 494-510 (Abstract Only).

Rosa, L T., et al., "Tripartite ATP-Independent Periplasmic (TRAP) Transporters and Tripartite Tricarboxylate Transporters (TIT): From Uptake to Pathogenicity", Frontiers in Microbiology, vol. 8,, 2018, 16 pgs.

Sacamboio, E. N. M., et al., "The transcriptional regulator NtrC controls glucose-6-phosphate dehydrogenase expression and polyhydroxybutyrate synthesis through NADPH availability in Herbaspirillum seropedicae", Scientific Reports, vol. 7, Article No. 13546, 2017, pp. 1-12.

Sadowski, M I., et al., "The sequence-structure relationship and protein function prediction", Current Opinion in Structural Biology 19, 2009, pp. 357-362.

Sanchez, A. M., et al., "Effect of overexpression of a soluble pyridine nucleotide transhydrogenase (UdhA) on the production of poly(3-hydroxybutyrate) in *Escherichia coli*", Biotechnol Prog., vol. 22, Issue 2, 2006, pp. 420-425 (Abstract Only).

Saur, U, et al., "The PEP-pyruvate-oxaloacetate node as the switch point for carbon flux distribution in bacteria", FEMS Microbiology Reviews, vol. 29, Issue 4, 2005, pp. 765-794.

(56) References Cited

OTHER PUBLICATIONS

Schlegel, H. G., et al., "Formation of the Dehydroganses for Lactate, Ethanol and Butanediol in the Strictly Aerobic Bacterium Alcaligene eutrophus", Microbiology, vol. 117, 1980, pp. 475-481.
Schobert, P, et al., "Unusual C3 and C4 metabolism in the chemoautotroph Alcaligenes eutrophus", Journal of Bacterialogy, vol. 159, Issue 1, 1984, pp. 167-172.
Schramke, et al., "Revisiting Regulation of Potassium Homeostasis in *Escherichia coli*: The Connection to Phosphate Limitation", Wiley MicrobiologyOpen, vol. 6, No. 3, 2017, pp. 1-16.
Schwartz, E, et al., "A proteomic view of the facultatively chemolithoautotrophic lifestyle of Ralstonia eutropha H16", Proteomics, vol. 9, Issue 22, 2009, pp. 5132-5142 (Abstract Only).
Seffernick, J L., et al., "Melamine Deaminase and Atrazine Chlorohydrolase: 98 Percent Identical but Functionally Different", Journal of Bacteriology, 183, 2001, pp. 2405-2410.
Segura, D, et al., "Inactivation of pycA, encoding pyruvate carboxylase activity, increases polybeta-hydroxybutyrate accumulation in Azotobacter vinelandii on solid medium", Appl Microbiol Biotechnol, pp. 65, Issue 4, 2004, pp. 414-418.
Sekar, B S., et al., "Co-production of hydrogen and ethanol from glucose in *Escherichia coli* by activation of pentose-phosphate pathway through deletion of phosphoglucose somerase (pgi) and overexpression of glucose-6-phosphate dehydrogenase (zwf) and 6-phosphogluconate", dehydrogenase ( gnd), Biotechnology for Biofuels, vol. 10, 85, 2017, 12 pgs.
Shang, et al., "Poly(3-hydroxybutyrate) Synthesis in Fed-batch Culture of Ralstonia Eutropha with Phosphate Limitation Under Different Glucose Concentrations", Biotechnology Letters, vol. 25, Issue 17, 2003, pp. 1415-14197.
Shulman, Andrew, et al., "Structural Determinants of Allosteric Ligand Activation in RXR Heterodimers", Cell, vol. 116, 2004, pp. 417-429.
Singh, et al., "Protein Engineering Approaches in the Post-Genomic Era", Curr Protein Pept Sci., 2017, pp. 1-11.
Slabu, et al., "Discovery, Engineering and Synthetic Application of Transaminase Biocatalysts", ACS Catalysis 7, 2017, pp. 8263-8284.
Smith, Temple, et al., "Comparison of biosequences", Advances in Applied Mathematics, 2(4), Dec. 1981, pp. 482-489.
Steinbuchel, A, et al., "A multifunctional fermentative alcohol dehydrogenase from the strict aerobe Alcaligenes eutrophus: purification and properties", Eur J Biochem, vol. 141, Issue 3, 1984, pp. 555-564.
Stokke, R, et al., "Biochemical characterization of isocitrate dehydrogenase from Methylococcus capsulatus reveals a unique NAD+-dependent homotetrameric enzyme", Arch Microbiol., vol. 187, Issue 5, 2007, pp. 361-370.
Sun, J, et al., "Involvement of glnB, glnZ, and glnD genes in the regulation of poly-3-hydroxybutyrate biosynthesis by ammonia in Azospirillum brasilense Sp7", Appl. Environ. Microbiol, vol. 68, Issue 2, 2002, pp. 985-988.
Sun, J, et al., "The ntrB and ntrC genes are involved in the regulation of poly-3-hydroxybutyrate biosynthesis by ammonia in Azospirillum brasilense Sp7", Appl. Environ. Microbiol., vol. 66, Issue 1, 2000, pp. 113-117.
Tan, Z, et al., "Activating phosphoenolpyruvate carboxylase and phosphoenolpyruvate carboxykinase in combination for improvement of succinate production", Appl. Environ. Microbiol., vol. 79, Issue 16, 2013, pp. 4838-4844.
Tang, et al., "Identification of Dehalobacter reductive Dehalogenases that catalyse dechlorination of chlorofom, 1,1,1-tricloroethane and 1,1-dicloroethane", Phil Trans R Soc B 368:20120318, 2013, pp. 1-10.
Uniprot database, entry AOAOU2WHGO, Mar. 2016, 4 pages.
Valderrama, J A., et al., "AccR is a master regulator involved in carbon catabolite repression of the anaerobic catabolism of aromatic compounds in *Azoarcus* sp. CIB", Journal of Biological Chemistry, vol. 289, Issue 4, 2014, pp. 1892-1904.
Vemuri, G N., "Physiological response of central metabolism in *Escherichia coli* to deletion of pyruvate oxidase and introduction of heterologous pyruvate carboxylase", Biotechnology and Bioengineering, vol. 90, Issue 1, 2005, pp. 64-76.
Vollbrecht, D, et al., "Excretion of Metabolites by hydrogen Bacteria III. D(-)-3-hydroxybutanoate", European J. Appl. Microbiol. Biotechnol, vol. 7, 1979, pp. 259-266.
Vollbrecht, et al., "Excretion of Metabolites by Hydrogen Bacteria I. Autotrophic and Heterotrophic Fermentations", European journal of applied microbiology and biotechnology, vol. 6, Issue 2, 1978, pp. 145-155.
Vollbrecht, et al., "Excretion of Metabolites by Hydrogen Bacteria II. Influences of Aeration, pH, Temperature, and Age of Cells", European Journal of Applied Microbiology and Biotechnology, vol. 6, Issue 2, 1978, pp. 157-166.
Vollbrecht, et al., "Excretion of Metabolites by Hydrogen Bacteria IV. Respiration Rate-dependent Formation of Primary Metabolites and of Poly-3-Hydroxybutanoate", European Journal of Applied Microbiology and Biotechnology, vol. 7, Issue 3, 1979, pp. 267-276.
Volodina, E, et al., "Characterization of propionate GoA-transferase from Ralstonia eutropha H16", Appl Microbiol, Biotechnol, vol. 98, Issue 8, 2014, pp. 3579-3589.
Wang, et al., "Poly(3-Hydroxybutyrate) Production with High Productivity and High Polymer Content by a Fed-Batch 23 Culture of Alcaligenes latus under Nitrogen Limitation", Applied and Environmental Microbiology, vol. 63, No. 9, Sep. 1997, pp. 3703-3706.
Wang, R, et al., "Isocitrate dehydrogenase from *Streptococcus mutans*: biochemical properties and evaluation of a putative phosphorylation site at Ser102", PLoS One, vol. 8, Issue 3, 2013, pp. e58918 (1-8).
Weinberg, Z, et al., "Identification of 22 candidate structured RNAs in bacteria using the Cmfinder comparative genomics pipeline", Nucleic Acids Research, vol. 35,, 2007, pp. 4809-4819.
Welden, et al., "Cation Transport in *Escherichia coli* Vii. Potassium Requirement for Phosphate Uptake", The Journal of General Physiology, vol. 50, No. 6, 1967, pp. 1641-1661.
Whisstock et al., "Prediction of protein function from protein sequence and structure", Quarterly Reviews of BioPhysics, vol. 36, Issue 3, pp. 307-340 (2003).
Winnen, B, et al., "The tripartite tricarboxylate transporter (TIT) family", Res. Microbiol, vol. 154, Issue 7, 2003, pp. 457-465.
Witkowski, A, et al., "Conversion of a β-Ketoacyl Synthase to a Malonyl Decarboxylase by Replacement of the Active-Site Cysteine with Glutamine", Biochemistry, 38, 1999, pp. 11643-11650.
Wu, M-C, et al., "A Novel Type II NAD+-Specific Isocitrate Dehydrogenase from the Marine Bacterium Congregibacte itoralis KT71", PLoS One., vol. 10, Issue 5, 2015, pp. 1-17.
Youngquist, et al., "Functional Genomics Analysis of Free Fatty Acid Production under Continuous Phosphate Limiting Conditions", J. Ind. Microbiol. Biotechnol., vol. 44, May 2017, pp. 759-772.
Zhang, M et al., Propagated Perturbations from a Peripheral Mutation Show Interactions Supporting WW Domain Thermostability, 2018, Structure. 26, 1474-1485. (Year: 2018).
Non-Final Rejection received for U.S. Appl. No. 16/372,106, mailed on Apr. 5, 2022, 33 Pages.
Yuzawa Satoshi et al., "Synthetic biology of polyketide synthases", Journal of Industrial Microbiology & Biotechnology, vol. 45, No. 7, Feb. 9, 2018, pp. 621-633.
Non-Final office action for U.S. Appl. No. 16/399,145 mailed on Jul. 27, 2023, 29 pages.
PTO STIC search in GenEmbl run on Jun. 27, 2022, pp. 1-6.
"aspartate aminotransferase family protein [Rhodobacteraceae bacterium CH30]", GenBank: RQW28969.1, Dec. 2, 2018, 2 pages.
Advisory Action received for U.S. Appl. No. 16/372,099, mailed on Feb. 22, 2022, 3 pages.
Advisory Action received for U.S. Appl. No. 16/372,106, mailed on Mar. 9, 2022, 3 pages.
Advisory Action received for U.S. Appl. No. 16/399,145, mailed on Mar. 4, 2022, 4 pages.
U.S. Appl. No. 16/372,083, Notice of Allowability mailed Sep. 22, 2021, 5 pages.
U.S. Appl. No. 16/398,351, Final Office Action mailed Jul. 2, 2021, 24 Pages.

(56) References Cited

OTHER PUBLICATIONS

Baltz et al. "Manual of Industrial Microbiology and Biotechnology", ASM Press, 2010, 4 Pages (Abstract).
Berg et al." Biochemistry 5th ed.", W H Freeman and Company, 2002, 1 Page (Abstract).
Cavalheiro JMBT et al. Poly(3-hydroxybutyrate) production by Cupriavidus necator using waste glycerol, Process Biochemistry, vol. 44, 2009, pp. 509-515.
Database UniProt [Online] Jul. 24, 2013 (Jul. 24, 2013), "SubName: Full=Acyl-ACP thioesterase ;", retrieved from EBI accession No. Uniprot: R7CHF5 Database accession No. R7CHF5.
Database UniProt, "RecName: Full=Thiopurine S-methyltransferase [ECO:0000256|HAMAPRule:MF_00812, ECO:0000256|SAAS:SAAS00896910}; EC=2.1.1.67; AltName: Full= Thiopurine methyltransferase ", EBI accession No. Uniprot: A0A1L8MA47 Database accession No. A0A1L8MA47, Mar. 15, 2017, 04 Pages.
Database UniProt,"RecName: Full=Thiopurine S-methyltransferase [ECO:0000256| HAMAPRule:MF_00812, ECO:0000256|SAAS:SAAS00896910}; EC=2.1.1.67; AltName: Full= Thiopurine methyltransferase " , EBI accession No. Uniprot: A0A009ZVV4 Database accession No. A0A009ZVV4, Jun. 11, 2014, 04 Pages.
Final office action received for U.S. Appl. No. 16/398,351, mailed on Feb. 28, 2022, 11 pages.
Final office action received for U.S. Appl. No. 16/398,401, mailed on Feb. 6, 2023, 25 pages.
Final Rejection received for U.S. Appl. No. 16/372,099, mailed on Dec. 21, 2021, 17 pages.
Final Rejection received for U.S. Appl. No. 16/372,106, mailed on Dec. 22, 2021, 32 pages.
Final Rejection received for U.S. Appl. No. 16/372,106, mailed on Oct. 4, 2021, 29 pages.
Final Rejection received for U.S. Appl. No. 16/399,145, mailed on Dec. 22, 2021, 20 pages.
Folsom, J.P. et al., "Physiological and Proteomic Analysis of Escherichia coli Iron-Limited Chemostat Growth," Journal of Bacteriology, vol. 196, No. 15, Aug. 2014, pp. 2748-2761,.
GenBank A6VKV4 GenBank 2012 pp. 1-3.
GenBank CAQ69169.1, 2015, pp. 1-2.
GenBank Q0K4C1, GenBank, 2006; p. 1.
GenBank Q0K5F4. 2006. GenBank. page 1 (Year: 2006).
GenBank Q0K790, GenBank, 2006; p. 1.
GenBank Q0K7M4. 2006. GenBank. page 1 (Year: 2006).
GenBank Q0KC80. 2006. GenBank. page 1 (Year: 2006).
GenBank Q2Z1A9. 2006. GenBank. page 1 (Year: 2006).
GenBank Q46WX6, GenBank, 2006; p. 1-2.
GenBank Q474V2, GenBank, 2006; p. 1-2.
GenBank Q8XWW2.1, 2015, pp. 1-2.

Harder et al., "Physiological responses to nutrient limitation", Annual Review of Microbiology, vol. 37, 1983, pp. 1-23.
KEGG Enzyme 1.6.1.1. Retrieved Feb. 22, 2022 (Year: 2022) pp. 1-2.
KEGG Enzyme 1.6.1.2. Retrieved Feb. 22, 2022 (Year: 2022) pp. 1-2.
KEGG Enzyme 7.1.1.1. Retrieved Feb. 22, 2022 (Year: 2022) pp. 1-2.
Kihlberg," The Microbe as a Source of Food" Annual Review of Microbiology, vol. 26, 1972, pp. 427-466.
Inui, M., et al., Metabolic Engineering of Corynebacterium glutamicum for Fuel Ethanol Production under Oxygen-Deprivation Conditions. 2004. J. Mol. Microbiol. Biotechnol., vol. 8, pp. 243-254.
Maqbool, A et al., "Multispecies: CmpA/NrtA family ABC transporter substrate-binding protein [Cupriavidus]", Retrieved from internet https://www.ncbi.nlm.nih.gov/protein/WP_010814804.1/, Mar. 20, 2023, 2 pages.
Non-Final Action received for U.S. Appl. No. 16/398,351, mailed on Jul. 5, 2022, 12 Pages.
Non-Final Action received for U.S. Appl. No. 16/398,401, mailed on Sep. 1, 2022, 32 pages.
Non-Final Rejection received for U.S. Appl. No. 16/398,401, mailed on Jun. 22, 2023, 18 pages.
Non-Final Rejection received for U.S. Appl. No. 16/398,401, mailed on Nov. 9, 2021, 38 Pages.
Notice of Allowance received for U.S. Appl. No. 16/372,099, mailed on Apr. 15, 2022, 11 pages.
Ogawa et al., "Role of Phosphoenolpyruvate in the NADP-Isocitrate Dehydrogenase and Isocitrate Lyase Reaction in Escherichia coli", Journal of Bacteriology, vol. 189, No. 3, Feb. 2007, pp. 1176-1178.
Response to Final Office Action for U.S. Appl. No. 16/372,099, filed Feb. 8, 2022, 9 pages.
Response to Final Office Action received for U.S. Appl. No. 16/399,145, filed on Feb. 22, 2022, 10 pages.
Response to Final Rejection for U.S. Appl. No. 16/372,106, filed on Feb. 16, 2022, 9 pages.
Response to Non-Final Office Action for U.S. Appl. No. 16/372,099, filed Oct. 7, 2021, 8 pages.
Stanbury et al. "Principles of Fermentation Technology", 3rd Edition, Aug. 31, 2016, 4 Pages.(Abstract).
U.S. Appl. No. 16/399,155, Non Final Office Action dated Jul. 15, 2019, 19 pages.
U.S. Appl. No. 16/399,155, Response filed Oct. 15, 2019 to Non-Final Office Action dated Jul. 15, 2019, 12 pages.
Uniprot database, entry A0AOU2WHG0, Mar. 2016, 4 pages.
Yonezuka, K. et al., "phosphonate C-P lyase system protein PhnG [Cupriavidus necator]", Retrived from internet https://www.ncbi.nlm.nih.gov/protein/KUE89182.1, Dec. 23, 2015, 2 pages.

* cited by examiner

MATERIALS AND METHODS FOR MANAGING AEROBIC GAS FERMENTATION

CROSS REFERENCE TO RELATED APPLICATION

The present application claims the benefit of U.S. Provisional Patent Application No. 62/650,575 filed Mar. 30, 2018, which is incorporated herein by reference for all purposes.

FIELD

The present disclosure generally relates to the control of dissolved oxygen concentration in aerobic biosynthesis. In particular, the present disclosure relates to the control of dissolved oxygen within a particular range and to control of the gaseous oxygen concentration in a fermenter headspace.

BACKGROUND

In gas fermentation, carbon-rich gases such as carbon dioxide, carbon monoxide and methane are converted by microorganisms into a wide range of products such as fuel, protein, and chemical compounds, for example, alcohols and organic acids. These products can be used by industries in the chemical, petrochemical, pharmaceutical, animal feed, environmental and agricultural sectors. Gas fermentation processes may utilize a variety of feedstocks including those sourced from domestic, industrial or agricultural waste, thereby reducing reliance on fossil sources of carbon and reducing emission of greenhouse gases. The gas fermentation generally operates at lower reaction temperatures and pressures when compared to high temperature and pressure chemical catalytic reactions.

Microorganisms grow under various engineering and physical conditions inside the fermenter such as agitation, mixing, aeration, pressure, shear, temperature and pH. Some microorganisms grow under anaerobic conditions while others grow under aerobic conditions. For aerobic reactions, air is generally used as the source of oxygen, but oxygen-enriched air or pure oxygen can also be used. It is generally preferable to operate at the highest possible oxygen concentration to maximise oxygen mass transfer and thereby optimise productivity. This is because the rate of oxygen mass transfer from the gas phase to the liquid phase is a known rate-limiting step for most aerobic microbial biosynthetic reactions.

Additionally, for any potentially flammable gas mixture outside of the fermenter, e.g., the gases dispersed within the fermenter broth (i.e., liquid phase), such as the fermenter headspace gas mixture, it is desirable to operate with the gaseous oxygen concentration safely below the Lower Oxygen Concentration (LOC) for flammability for the gaseous composition. The DO and gaseous oxygen concentration in the headspace are difficult to control, especially as pressure is increased above atmospheric pressure and as oxygen solubility increases.

Therefore, the need exists for improved control and maintenance of DO concentration with a range that is acceptable for the microorganism while achieving acceptable productivity, safety, capital cost (capital efficiency), and operating cost.

SUMMARY

In some aspects, the present disclosure is directed to a method for controlling dissolved oxygen concentration in a continuous aerobic gas fermentation process, the method comprising: a) providing a microorganism to a fermenter; b) introducing at least two feed streams to the fermenter, wherein at least one feed stream comprises gaseous oxygen and wherein at least one feed stream comprises a flammable gas and optionally oxygen at an oxygen concentration below the limiting oxygen concentration (LOC); c) measuring the dissolved oxygen concentration in at least one location in the fermenter; d) measuring the gaseous oxygen concentration in the headspace; and e) controlling the dissolved oxygen concentration in the fermenter to be greater than a minimum dissolved oxygen concentration required for the microorganism to function and less than the dissolved oxygen concentration above which the gaseous oxygen concentration in the headspace exceeds the limiting oxygen concentration (LOC). The microorganism is considered to function if the microorganism has a specific oxygen uptake rate of at least 1 mmol oxygen/(g dry cell weight)/hour. In certain aspects, the at least one feed stream comprising a flammable gas and oxygen does not include the at least one feed stream comprising gaseous oxygen, e.g., the at least one feed stream comprising the flammable gas does not comprise oxygen. In some embodiments, the dissolved oxygen concentration is controlled by regulating the oxygen mass transfer rate by regulating at least one of: i. the flow rate of the at least one gaseous stream comprising oxygen; ii. the concentration of oxygen in the at least one gaseous stream comprising oxygen; iii. the amount of gas holdup as gas bubbles within the fermenter; iv. the size of the gas bubbles within the fermenter; and v. one or more physical properties of the fermentation broth affecting oxygen mass transfer rate. The physical properties can be selected from group consisting of surface tension, viscosity, density, and temperature. In some embodiments, the flammable gas comprises hydrogen. In some embodiments, at least one of the at least two feed streams comprises carbon dioxide. The flow rate of the at least one gaseous stream comprising oxygen may be regulated by adjusting the total flow rate of the at least one gaseous stream and/or by adjusting the oxygen concentration in the at least one gaseous stream comprising oxygen. The fermenter may be selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters. The fermenter may be a non-stirred fermenter. In some embodiments, the fermenter is not mechanically agitated. The microorganism may be dependent on chemoautotrophic metabolism/RUBISCO. The microorganism may be a RUBISCO-containing microorganism. The microorganism may be selected from non-pathogenic members of the genera *Ralstonia, Wausteria, Cupriavidus, Alcaligenes, Burkholderia* or *Pandoraea*. In some aspects, the microorganism is *C. necator* or *C. metalliduruns*. The fermenter may be operated at a pressure above atmospheric pressure. The method may further comprise: f measuring gaseous oxygen concentration in headspace of the fermenter; and g. controlling the gaseous oxygen concentration to be less than 75% of the limiting oxygen concentration (LOC) of the gaseous mixture in the headspace of the fermenter. The fermenter may comprise at least two oxygen addition inlets. The at least one feed stream comprising gaseous oxygen may be an air feed stream, an oxygen-enriched air stream, or a pure oxygen stream. The dissolved oxygen concentration may be controlled to be at a value below the Transitional DO concentration.

In some aspects, the present disclosure is directed to a fermenter system for an aerobic gas fermentation process, the system comprising: a. a fermenter comprising at least two oxygen addition points; b. a microorganism in the fermenter; and c. at least two control loops, wherein at least one control loop measures and controls dissolved oxygen content in a fermentation liquid in the fermenter and wherein at least one control loop measures and controls gaseous oxygen concentration in a headspace of the fermenter. In some aspects, the system comprises at least two fermenters in series. In other aspects, the system comprises at least two fermenters in parallel. The fermenter may be selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters. The fermenter may be operated at a pressure above atmospheric pressure.

BRIEF DESCRIPTION OF THE DRAWINGS

The present disclosure will be better understood in view of the appended non-limiting figures, in which.

DETAILED DESCRIPTION

Figure 1:
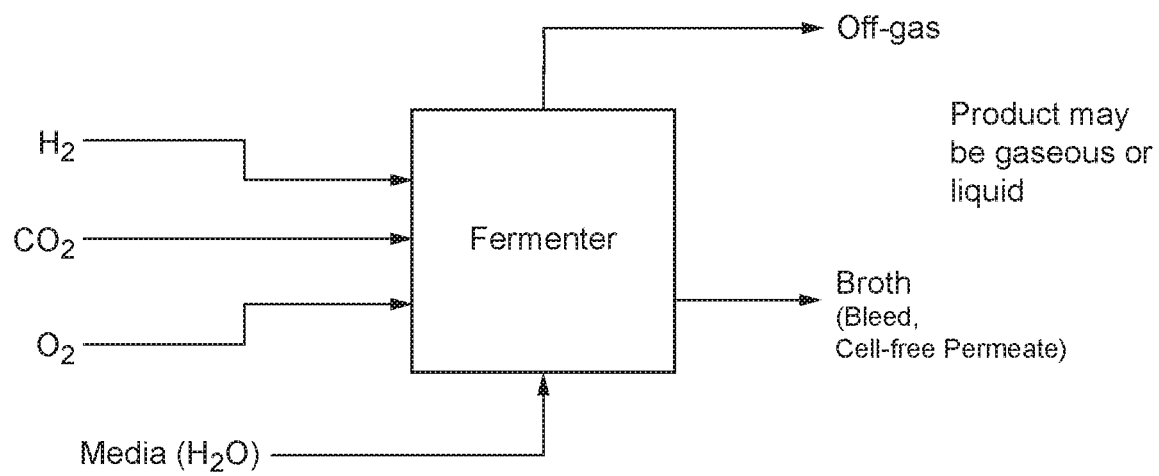
FIG. 1 shows a block diagram of a gas fermentation process having three gas feeds in accordance with an embodiment of the present disclosure.

The present disclosure is directed to materials and methods for managing aerobic biosynthesis, including methods of controlling oxygen concentration. Certain organisms, such as *Cupriavidus necator*, cease to function, or function at very low rates, below a minimum dissolved oxygen (DO) concentration because they are no longer able to metabolize oxygen at a minimal rate permitting growth and product generation. In addition, these organisms display growth inhibition and reduced oxygen uptake rate (OUR) when DO is above a certain concentration. Accordingly, control of DO concentration within a particular range is important to ensure improved or optimal growth of and productivity by the organism. DO concentration is also balanced with, and in equilibrium with, the oxygen concentration in the gaseous headspace of the fermenter in which the aerobic biosynthesis occurs. When the headspace is maintained at a non-flammable composition, the upper control limit for the oxygen concentration in the gaseous headspace corresponds to the Limiting Oxygen Concentration (LOC) for flammability for the composition. The minimum DO concentration is the lower control limit for the fermenter.

In some aspects, the oxygen concentration that is controlled is a dissolved oxygen concentration. The method for controlling dissolved oxygen concentration comprises: a. providing a microorganism to a bioreactor, e.g., a fermenter, and introducing at least two feed streams to the reactor. At least one of the feed streams comprises gaseous oxygen and at least one of the feed streams comprises a flammable gas (e.g., hydrogen) and optionally comprises oxygen at a concentration below the limiting oxygen concentration (LOC) for flammability. The method further comprises measuring the dissolved oxygen concentration in at least one location in the fermenter and controlling the dissolved oxygen concentration in the fermenter. The dissolved oxygen concentration is controlled to be at least equal to a minimum value for the microorganism to function and to be less than a value that results in a gaseous oxygen concentration in the headspace being at or above the LOC for flammability of the gaseous mixture in the headspace. The method can also comprise measuring the gaseous oxygen concentration in the headspace of the fermenter and controlling the dissolved oxygen concentration to be less than the amount above which the gaseous oxygen concentration in the headspace exceeds the LOC.

In further aspects, the present disclosure is also directed to measuring and controlling the gaseous oxygen concentration in the headspace of the fermenter in which the aerobic biosynthesis occurs. This gaseous oxygen concentration in the headspace is controlled to be less than the limiting oxygen concentration (LOC) for flammability of the gaseous mixture in the headspace, e.g., less than 85% of the LOC.

In still further embodiments, the present disclosure is directed to a fermenter system for an aerobic gas fermentation process. The system comprises a fermenter comprising at least two gas addition points, e.g., oxygen addition points. A microorganism is provided in the fermenter. The system further comprises at least two control loops, wherein at least one control loop measures and controls dissolved oxygen content in a fermentation liquid in the fermenter and at least one control loop measures and controls gaseous oxygen concentration in a headspace of the fermenter.

Conventionally, the DO concentration and the LOC are controlled at atmospheric pressure in stirred fermenters, such as CSTRs, where DO concentration tends to be more uniform throughout the fermentation liquid, due to back-mixing in a CSTR. The operation of a continuous aerobic process with pressures above atmospheric pressure and/or with little to no mechanical agitation (e.g., in non-stirred bioreactors with little back-mixing) has not been achieved, due at least in part to difficulties in maintaining a uniform DO while operating safely below the LOC.

The inventors discovered that in order to operate below the limiting oxygen concentration (LOC) for flammability but not let oxygen levels drop too far, the mass transfer rate of oxygen can be regulated. The inventors have discovered that to maintain DO concentrations and optimize the oxygen uptake rate (OUR) in a capitally efficient fermenter, they could control the oxygen concentrations by using one or more of 1. multiple oxygen injection points, 2. multiple serial flow reactors, 3. microbubble generation, 4. maintenance of a relatively high gas hold-up, and 5. one or more DO concentration measurement points and control methods to maintain DO concentration and gaseous oxygen concentration within limits and optimize OUR, e.g., control of DO concentration on left side, or right side, or both sides of the OUR vs. DO concentration curve, discussed further herein.

The methods for controlling oxygen concentrations during biosynthesis, and the fermenter itself, are described below.

Microorganism

A microorganism is provided to the fermenter described herein in order for the aerobic biosynthesis to occur. For aerobic reactions, air is generally used as the source of oxygen, but oxygen-enriched air or pure oxygen can also be used. It is generally preferable to operate at the highest possible oxygen concentration in the dispersed gas phase within a fermenter to maximise oxygen mass transfer and thereby optimise productivity. This is because the rate of oxygen mass transfer from the gas phase to the liquid phase is a known rate-limiting step for most aerobic microbial biosynthetic reactions. A consequence of having high oxygen concentrations (such as >6 vol % oxygen in the dispersed gas phase in streams that are rich in hydrogen) is that any unreacted oxygen in the fermenter headspace and effluent gas stream can result in the formation of unsafe flammable mixtures when flammable gases (e.g., hydrogen), flammable volatile organic products, or intermediates are present.

In some aspects, the microorganism is dependent on chemoautotrophic metabolism/RUBISCO. In still further aspects, the microorganism is a RUBISCO-containing microorganism. As a non-limiting example, the microorganism may be *Cupriavidus necator* (*C. necator*) or an organism with properties similar thereto. *C. necator* (previously called *Hydrogenomonas eutrophus*, *Alcaligenes eutropha*, *Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. Additional properties of *C. necator* include microaerophilicity, copper resistance (Makar and Casida; 1987), bacterial predation (Byrd et al., 1985; Sillman & Casida, 1986; Zeph & Casida, 1986) and polyhydroxybutyrate (PHB) synthesis. In addition, the cells have been reported to be capable of both aerobic and nitrate dependent anaerobic growth. A nonlimiting example of a *C. necator* organism useful in the present disclosure is a *C. necator* of the H16 strain. In one nonlimiting embodiment, a *C. necator* host of the H16 strain with at least a portion of the phaC1AB1 gene locus knocked out (ΔphaCAB), as described in U.S. patent application Ser. No. 15/717,216, teachings of which are incorporated herein by reference, is used. The organism may be selected from non-pathogenic members of the genera *Ralstonia*, *Wausteria*, *Cupriavidus*, *Alcaligenes*, *Burkholderia* or *Pandoraea*. In some embodiments, the microorganism is *Cupriavidus necator*, *Cupriavidus metallidurans*, *Cupriavidus oxalaticus*, *Cupriavidus alkaliphilus*, *Cupriavidus basilensis*, *Cupriavidus pinatubonensis*, *Cupriavidus taiwanensis*, *Cupriavidus pampae*, *Cupriavidus pauculus*, *Ralstonia pickettii*, *Ralstonia* sp. DB3, or *Ralstonia* sp. PBA.

In certain aspects, the microorganism is *C. necator*, a microorganism shown to exhibit oxygen inhibition at elevated DO concentrations. This oxygen inhibition has been reported by others to affect only polyhydroxybutyrate (PHB) production, and not the growth of the organism. The inventors, however, have discovered that the oxygen inhibition of *C. necator* also affects the growth of the organism, as described below.

Unlike most other species, organisms such as *Cupriavidus necator* display growth inhibition when DO is above a certain concentration. This was found through kinetic studies of H16 WT *Cupriavidus necator*, which showed oxygen inhibition on growth rate at dissolved oxygen concentrations of greater than ~1 mg/L. Loss of growth and reduction in specific oxygen uptake rate (OUR) was observed when DO concentration increased. This phenomenon is even more important when operating at elevated pressures as the solubility of oxygen and the resultant DO concentration increase, and/or when operating in continuous reactors with little or no mechanical agitation where the DO can change throughout the fermenter. Accurate dissolved oxygen measurements are important for determining where the gas fermentation process is operating, relative to oxygen concentration limits, and to understanding the impact of process control actions. It is desirable to maintain the DO concentration at levels sufficient to maintain optimal growth and OUR, even at pressures above atmospheric pressure.

Feed Streams

As described above, oxygen is needed for the aerobic biosynthesis to occur and is introduced to the fermenter via a feed stream. In order to introduce gaseous feed streams into the fermenter in a safe manner, at least two different continuous streams of feeds are used. At least one continuous stream comprises a flammable gas (e.g., hydrogen) and at least one feed stream comprises gaseous oxygen. The at least one feed stream comprising a flammable gas may optionally comprise oxygen at a concentration below the limiting oxygen concentration (LOC) for flammability and may optionally comprise all or a portion of the $CO_2$ gas feed. The at least one continuous stream comprising oxygen may comprise at least 15 wt. % oxygen and may be an air feed stream, an oxygen-enriched air stream, or a pure oxygen stream. Such a feed stream would not contain hydrogen gas, or would contain hydrogen gas at a concentration below the lower flammability limit for hydrogen, but may optionally comprise all or a portion of the $CO_2$ gas feed. Each gas feed stream is introduced into the fermenter by means described elsewhere herein. By separating the hydrogen and a large portion of the oxygen into separate feed streams, a flammable gas mixture cannot form in the feed system and gas mixtures containing both hydrogen and oxygen are present only in the small-volume gas bubbles within the fermentation broth and within the headspace and effluent gas stream. In some aspects, the gaseous oxygen concentration in the dispersed gas phase bubbles within the broth may be at an increased value as compared to the gaseous oxygen concentration in the bulk gas phase, e.g., the headspace. In certain aspects, the gaseous oxygen concentration in the dispersed gas phase bubbles within the broth is above the LOC.

Fermenter

As described herein, the temperature and pressure parameters of the fermenter may vary, e.g., at pressures from below atmospheric pressure to above atmospheric pressure, and at temperatures from 20 to 50° C. The type of fermenter to be used may be selected based on the desired operating temperature and pressure, as well as on additional factors. Examples of the additional factors include whether mechanical agitation or stirring is desirable, whether the microorganism will be immobilized, and how many oxygen addition points are desired. Examples of fermenters, such as types of gas fermenters include single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

The fermenter may include one or more sensors configured to measure one more parameters of the environment and/or culture within the fermenter. The sensors may, for example, include one or more temperature sensors, pH sensors, pressure sensors, dissolved oxygen sensors, foaming sensors, optical density sensors, and other enzymatic, near-infrared, or mid-infrared sensors. The operating conditions of the fermenter can be measured and controlled as needed to carry out processes within the fermenter, and in some aspects the measuring and controlling involves measurements from the one or more sensors.

As described herein, the fermenter may interact with at least one control loop to measure and control dissolved oxygen concentration. The fermenter may interact with an additional control loop to measure and control gaseous oxygen concentration in the headspace of the fermenter. The control loops may use feed forward controls, feedback controls, and combinations thereof.

Figure 3A:
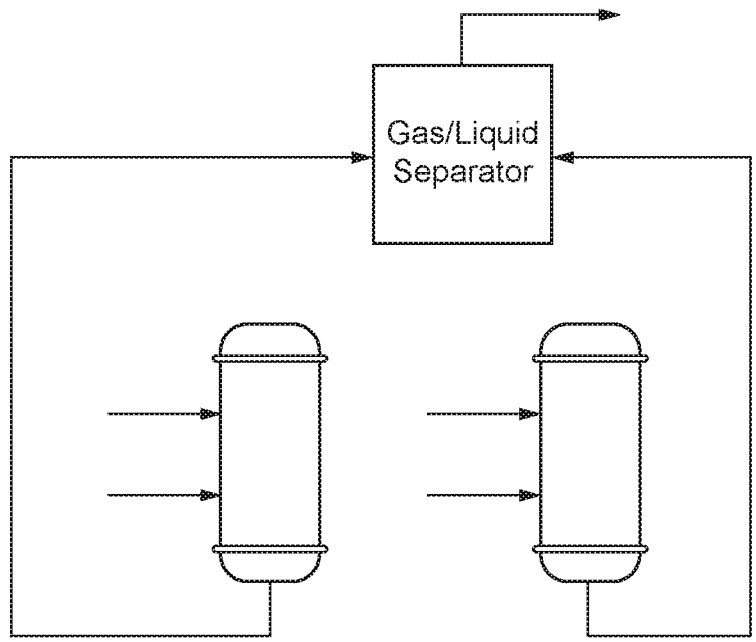
FIGS. 3A and 3B show fermenters in parallel and series configurations in accordance with embodiments of the present disclosure.
Figure 3B:
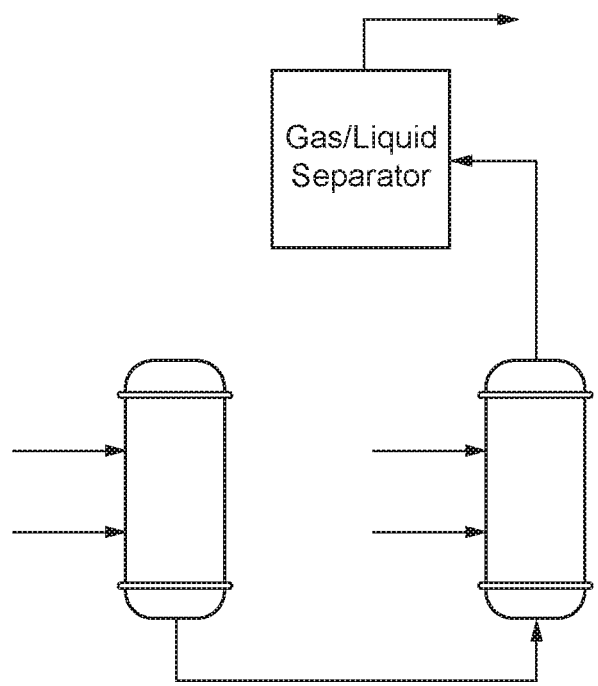

In some aspects, more than one fermenter is used. The fermenters may be arranged in parallel, as shown in FIG. 3a, or in series, as shown in FIG. 3b. When arranged in series, the control loops (not shown) that measure and control dissolved oxygen concentration at various locations (elevations) regulate the flow of the gaseous feed stream comprising oxygen immediately preceding the dissolved oxygen concentration measurement location.

In some embodiments, the gauge pressure of the fermenter is maintained within a desired range to influence factors such as gas solubility within the fermenter. The gauge pressure within the fermenter can be, for example, from 1 bar to 10 bar, e.g., from 1.1 bar to 6.4 bar, from 1.9 bar to 7.3 bar, from 2.8 bar to 8.2 bar, from 3.7 bar to 9.1 bar, or from 4.6 bar to 10 bar. In terms of upper limits, the fermenter gauge pressure can be less than 10 bar, e.g., less than 9.1 bar, less than 8.2 bar, less than 7.3 bar, less than 6.4 bar, less than 5.5 bar, less than 4.6 bar, less than 3.7 bar, less than 2.8 bar, or less than 1.9 bar. In terms of lower limits, the fermenter gauge pressure can be greater than 1 bar, e.g., greater than 1.9 bar, greater than 2.8 bar, greater than 3.7 bar, greater than 4.6 bar, greater than 5.5 bar, greater than 6.4 bar, greater than 7.3 bar, greater than 8.2 bar, or greater than 9.1 bar. Higher gauge pressures, e.g. greater than 10 bar, are also contemplated. Gauge pressure measured in bars may also be referred to as bar(g).

Control Parameters for Oxygen Concentrations

As described herein, oxygen concentration in the fermenter is controlled to be within specified ranges. The dissolved oxygen concentration is controlled to be at least a minimum value required for the microorganism to function. The microorganism is considered to function if it has a specific oxygen uptake rate of at least 1 mmol oxygen/(g dry cell weight)/hour, e.g., at least 2 mmol oxygen/(g dry cell weight)/hour, at least 3 mmol oxygen/(g dry cell weight)/hour, at least 4 mmol oxygen/(g dry cell weight)/hour, at least 5 mmol oxygen/(g dry cell weight)/hour, at least 6 mmol oxygen/(g dry cell weight)/hour, at least 7 mmol oxygen/(g dry cell weight)/hour, at least 8 mmol oxygen/(g dry cell weight)/hour, at least 9 mmol oxygen/(g dry cell weight)/hour, or at least 10 mmol oxygen/(g dry cell weight)/hour. The minimum value is required because the microorganism is aerobic and requires a certain amount of oxygen, below which the microorganism will not be capable of growing or generating product, and the process will not be economical.

The concentration of gaseous oxygen in the headspace of the fermenter is also controlled to operate safely below the LOC. To provide a safety measure for process upsets, the gaseous oxygen concentration in the headspace may be measured and controlled to be less than the LOC, e.g., less than a desired safety margin below the LOC. In some aspects, the gaseous oxygen concentration in the headspace may be less than 85% of the LOC, e.g., less than 80%, less than 75% or less than 70%. In some aspects, the gaseous oxygen concentration in the headspace is controlled to be within 65 to 85% of the LOC. In some aspects, the LOC is approximately 5.9 vol % oxygen in the gaseous mixtures outside of the fermentation broth, though it may vary from 5 to 6 vol. %, depending on the gaseous mixture.

In addition to operating at the desired DO concentration and LOC values, it is desirable to maximize economic value considering productivity, capital cost, and operating cost. From a process engineering perspective, there are natural conflicts to manage. Ideally, the oxygen concentration would be maximized for mass transfer but minimized for process safety.

Dissolved Oxygen Concentration

The DO is measured and then controlled to be greater than a minimum DO concentration required for the microorganism to function, e.g., at least 1 mmol oxygen/(g dry cell weight)/hour. The DO concentration is controlled by regulating the oxygen mass transfer rate to the fermenter. Because of the relatively low aqueous solubility of oxygen in water, the oxygen mass transfer rate is a rate limiting factor for cell growth and production in the fermenter.

The at least one feed stream comprising gaseous oxygen may be introduced into the fermenter by a suitable device in order to create microbubbles and enhance the gas-liquid interface between gas phase and bulk liquid. The location of the feed point may vary, but may generally be near the bottom of the fermenter, assuming a vertical fermenter. An additional oxygen addition point may be further along or up the fermenter (assuming a vertical fermenter), but below the broth surface. In some aspects, the additional oxygen addition point may be equidistant from the first oxygen addition point and the surface of the broth. The DO controller for measuring the DO may be located near the first oxygen addition point (first DO controller) to allow for regulation of the oxygen addition rate at this first point. Additional DO controllers, e.g., a second DO controller, may be near the additional oxygen addition point to allow for regulating the oxygen addition at this additional point. The second DO controller may also interact with the first DO controller to trim the oxygen addition rate at the first oxygen addition point, particularly if the second DO controller is not able to maintain the DO concentration at the additional oxygen addition point. As more oxygen addition points are included, more DO controllers may be included, which may interact with each other and with the first and second DO controllers.

Additionally, gas-liquid mass transfer depends on the reactor configuration. There are seven general steps of mass transfer of the gases to the reaction site.

1. Diffusion through the bulk gas within a gas bubble to the gas-liquid interface.
2. Movement across the gas-liquid interface.
3. Diffusion of the solute gas through the relatively unmixed liquid region (film) adjacent to the bubble and into the well-mixed bulk liquid.

4. Transport of the solute gas through the bulk liquid to the stagnant film surrounding the cells.

5. Transport through the second unmixed liquid film associated with the cells.

6. Transport across the cell membrane.

7. Transport through the cell to the reaction site.

During aerobic biosynthesis, oxygen is needed for the microorganism to function, e.g., to grow and/or generate product. For example, *C. necator* is aerobic and will shut down at low DO concentration because oxygen is required for intracellular reactions. The soluble hydrogenases (SH) are enzymes that catalyse the oxidation of molecular hydrogen into protons and electrons, typically in the form of nicotinamide adenine dinucleotide (NADH). Namely, the SHs produce the energy and reducing equivalents for supporting growth of *C. necator*. The SHs are sensitive to the oxygen concentration. If the oxygen concentration is too high, their cofactor molybdenum becomes oxidised and if the oxygen concentration becomes too low, the SH can no longer regenerate NADH or ATP fast enough, and the organism shuts down.

The NADH generated by the SHs is necessary to drive carbon fixation via the Calvin-Benson Bassham cycle, which is the main pathway for carbon fixation when *C. necator* is grown under $CO_2/H_2$. Carbon dioxide and oxygen compete for the same active site and therefore compete for access to RubisCO. RubisCO's affinity for carbon dioxide is much higher than its affinity for oxygen. Thus, fixation of carbon dioxide typically exceeds fixation of oxygen, even though atmospheric carbon dioxide levels are about 0.035 vol % $CO_2$ whereas atmospheric oxygen concentration is about 21 vol % 02. Therefore, as the oxygen concentration decreases, the energy efficacy of carbon dioxide fixation increases.

The optimum activities for the soluble hydrogenases and RubisCO occur at different concentrations of dissolved oxygen and the minimum oxygen concentration needs to be carefully chosen.

Kinetic studies of H16 WT *Cupriavidus necator*, however, show oxygen inhibition on growth rate at dissolved oxygen concentrations of greater than ~1 mg/L. Loss of growth and reduced specific oxygen uptake rate (OUR) was observed when dissolved oxygen concentration increased. The maximum specific OUR occurs at a DO concentration herein referred to as the Transitional DO Concentration. Accurate dissolved oxygen measurements are important to knowing where the gas fermentation process is operating, relative to oxygen limits, and specifically relative to the Transitional DO concentration.

Gaseous Oxygen Concentration in Headspace

The upper limit for gaseous oxygen concentration in the headspace of the fermenter is limited by safety considerations. Typically, the literature quotes a ratio of 7:1:1 or 8:1:1 for $H_2/CO_2/O_2$ (hydrogen/carbon dioxide/oxygen) for the initial gas mixture for optimum growth/production conditions for gas fermentation for *C. necator* (Ishizaki et al 2001), although this ratio may vary depending on adjustments and reaction needs. Generally, however, this means that the hydrogen/oxygen ratio is within the flammable range for hydrogen and oxygen gas concentrations. The critical oxygen concentration when mixed with hydrogen with carbon dioxide as a diluent is 5.9 vol % (Jones and Kenny, 1935). Therefore, the Limiting Oxygen Concentration (LOC) of 5.9 vol % is here defined to be the minimum oxygen concentration at which a flammable gaseous mixture may form with gas fermentation process mixtures according to the present disclosure. These gas fermentation process mixtures are those which result in an oxygen, nitrogen, hydrogen, carbon dioxide and water vapour mixture in the headspace of the fermenter. Temperature and pressure conditions in the fermenter may also influence the relative concentration of components in the headspace. The fermenter is therefore operated below the LOC of 5.9 vol % oxygen. In order to maintain a safety margin, the fermenter may be operated within 70% to 80% of the LOC, or even less than 70%. In some aspects, the gaseous oxygen concentration in the headspace is controlled to be from 3.5 to 4.5 vol. % oxygen, e.g., from 3.75 to 4.25 vol. %, from 3.85 to 4.15 vol. %, from 3.95 to 4.05 vol. %, or approximately 4 vol. % oxygen. The fermenter effluent gas also has the same LOC.

Control of the Oxygen Concentrations

1. Multiple Oxygen Addition Points

In order to maintain the DO and LOC within the desired ranges, there may be two or more oxygen addition points, e.g., three or more, four or more, five or more, or six or more. As more oxygen addition points are included in the fermenter, the more constant the DO concentration may be throughout the fermentation liquid. For example, in a vertical column fermenter, such as a gas-lift fermenter, the DO concentration may be maintained vertically. As more oxygen addition points are added, however, the complexity and cost of the reactor design increases.

The oxygen addition points to the fermenter need not be linearly spaced and may be spaced on more than one side of the fermenter. The feed stream comprising oxygen may be delivered by a pipe that extends through the fermenter wall and terminates with some type of gas distribution device as described herein, e.g., a sparger. This allows for the feed stream to be distributed across the fermenter diameter.

Assuming a vertical fermenter, the feed stream comprising oxygen may be added at the bottom of the fermenter. In some aspects, the feed stream is air, oxygen-enriched air, or pure oxygen. The oxygen concentration may therefore be greater at the bottom of the fermenter than at the top of the fermenter. Oxygen addition points above the initial feed stream comprising oxygen allow for the DO concentration to be controlled to be more uniform throughout the fermentation liquid. In some embodiments, the feed stream that is free of gaseous oxygen may be introduced at the bottom of the fermenter and the feed stream comprising oxygen may be added above this point. Further oxygen addition points up the column in combination with adding the feed stream free of gaseous oxygen allows for more uniform DO through the fermentation liquid. The feed stream that is free of oxygen includes a flammable component, e.g., hydrogen or combinations of carbon dioxide and hydrogen. The mass transfer rate may be staged along the length of the column (whether vertical or horizontal), and oxygen addition points may be chosen accordingly.

The oxygen may be added gradually, along multiple microbubble generation modules along the length of the fermenter. This set-up allows for gradual oxygen addition which improves the ability to operate below the LOC, though it is balanced with the oxygen mass transfer rate. The oxygen addition to each module may be individually controlled based on measurements of the DO concentration.

2. Serial Reactors

When more than one fermenter is used, the fermenters may be placed in series or in parallel. Series reactors are advantageously more configurable than parallel reactors and thus allow operational flexibility. When in series, the reactors are two (or more) physically contained vessels. In a continuous process, serial reactors allow for the design of modular conditions. The use of serial reactors allows the occurrence of different conditions/phases e.g. different temperatures, salt control, or different ratios of oxygen feed. Serial reactors allow for each vessel to have different conditions, allowing for managing conditions in series reactors more so than in parallel reactors. Use of serial reactors gives more control points and more flexibility in the management of the system, e.g., more flexibility in managing gas circulation rate, pressure operation, salt control, different temperatures, different ratios of oxygen feed. Serial reactors are advantageously more configurable than parallel reactors.

Parallel fermenters may be used if fluid velocity is too high (e.g., pressure drop is too high) for a single fermenter having a practical maximum diameter. Series fermenters could be used if high fluid velocity is not an issue and there is a desire for a longer reaction path with more gas injection/dispersion zones and that path is longer than a practical height of a single fermenter.

The number of reactors in series and/or in parallel is limited by cost considerations. Generally, two to three reactors in series or in parallel may be used.

3. Gas Hold-Up

The volume fraction of gas phase in the gas-liquid dispersion is called gas hold-up and it determines the residence time of the gas in the liquid phase as well as affecting the gas-liquid interfacial area available for mass transfer. The gas hold-up is dependent on the gas superficial gas velocity (UG) and it is also a function of reactor geometry. The velocity of liquid circulation is controlled by the gas holdup and superficial gas velocity. The gas velocity also depends on the bubble size, viscosity of liquid and operating pressures.

The gas hold-up is itself controlled through bubble size and methods of generation. For example, the speed of the movement of the bubbles plays a factor and it is important to prevent the bubbles from moving too quickly otherwise they might coalesce too quickly. In addition, the properties of the broth need to be conducive to the formation and stability of small gas bubbles or microbubbles. For broth containing *C. necator* H16 WT that is not inherently foaming, a surfactant may be added, such as TWEEN® 20 polysorbate non-ionic surfactant, to achieve and maintain high gas hold-up and small gas bubbles. While at the broth upper surface, where the gas bubbles disengage from the broth, anti-foaming agent may be added to suppress foam carryover into the headspace and gas effluent stream. A proper balance of the amount of surfactant addition and anti-foaming agent addition may be reached to achieve and maintain high gas hold-up and suppress excessive surface foaming. For modified strains of *Cupriavidus necator* that produce extracellular products that have surfactant characteristics, a surfactant may not be included.

The gas hold-up (i.e. the amount of gas held as dispersed gas bubbles in the liquid phase) may be controlled because if there is too much gas in the liquid phase, there will be too much foaming and if there is too little gas in the liquid phase, there will be insufficient oxygen mass transfer. Increasing the mass transfer of gases can be achieved, for example, by increasing the operating pressure and/or by decreasing bubble size (since this increases the contact area).

To decrease bubble size, the gas mixture should be introduced into the fermenter by a suitable device in order to create microbubbles or other small bubbles and enhance the gas-liquid interface between gas phase to bulk liquid.

In a gas fermenter, the transfer rate of gases such as oxygen into the liquid (broth) phase is controlled by the liquid-phase mass-transfer coefficient ($k_L$), the total interfacial surface area available for mass transfer (a), the dissolved gas concentration at the gas-liquid interface (C*) that is in equilibrium with the gas concentration in the gas phase, and the dissolved gas concentration within the bulk of the liquid (C). Separate determination of mass-transfer coefficient ($k_L$) and gas-liquid interfacial area (a) is difficult to evaluate and sometimes impossible. The combined term of kLa, the volumetric mass-transfer coefficient, is usually reported rather than just mass-transfer coefficient ($k_L$). For oxygen, the oxygen mass transfer rate (OTR) is expressed as $$OTR = k_L a^* (DO^* - DO) \quad \text{i)}$$

where DO* is the dissolved oxygen concentration at the gas-liquid interface, which is in equilibrium with the oxygen concentration within the gas phase (i.e., gas bubble), and DO is the dissolved oxygen concentration within the bulk of the liquid (broth). At steady-state operation, oxygen mass transfer rate (OTR) must equal oxygen uptake rate (OUR) for the system.

The volumetric mass transfer coefficient ($k_L a$) is the rate of gas transfer across the gas-liquid interface per unit of driving force. The volumetric mass transfer coefficient is influenced by the bubble size which changes the specific surface area (a) and also depends on the mass transfer coefficient $k_L$. A decrease in bubble size will increase the specific interfacial area and therefore increase the volumetric mass transfer coefficient. The size of the gas bubbles can be reduced by using suitable aeration devices. The $k_L a$ is a function of gas bubble diameter, viscosity of liquid surface tension of medium, mixing and Reynolds number.

In aerobic bioprocess applications, oxygen transfer is one of the important parameters in scale up studies. The gas holdup is also an important parameter because it directly influences the volumetric mass transfer rate ($k_L a$). The main limiting step for the transport of the gas molecule from the bulk gas to the intracellular content is the interface at the gas-liquid film. The rate of mass transfer is directly proportional to the area available and the driving force for the transfer process.

The oxygen mass transfer rate may be regulated by various means. In some aspects, oxygen flow rate to the fermenter by be adjusted, either by total flow rate of the at least one feed stream comprising oxygen, or by oxygen concentration in the at least one feed stream comprising oxygen. In further aspects, the gas holdup may be adjusted, e.g., the amount of oxygen within the fermentation broth. In still further aspects, gas bubble size may be adjusted, e.g., the gas-liquid interfacial surface area for the oxygen mass transfer may be adjusted relative to the oxygen gas volume. In yet further aspects, physical properties of the fermentation broth affecting the oxygen mass transfer rate may be adjusted. Physical properties affecting oxygen mass transfer rate include, for example, surface tension, viscosity, density, and temperature.

4. Microbubble Generation

To improve the $k_L a$ the process can be operated to produce gas bubbles having a size (e.g., diameter) that is as small as possible, thereby increasing the specific surface area and increasing mass transfer of the gas into the liquid phase. There are several microbubble generators available, for example, membranes, cavitating pumps, venturi nozzles and sintered blocks.

In a cross-flow membrane microbubble generator, a compressed gas is introduced into a chamber via a membrane and the bubbles formed on the surface of the membrane are cut off by the cross flow entry and liquid. This arrangement (e.g., from D&B Tech, Spain) produces very fine bubbles and is suitable for small scale systems. Advantages of this system include: generation of microbubbles below 100 micron diameter, ease of assembly, the option to sterilize the membrane with steam, and the ability to adjust the flow rates of gas and liquid. There are, however, disadvantages, including fouling/blockage of the membrane with time, potentially low gas flow rates, and a requirement for an external pump for the cross flow of water.

In a centrifugal pump/microbubble generator, the pumps pull air/gas within the broth into the pump suction and the high rotation and shear from the pump impeller breaks the gas bubbles and provides a jet of very fine bubbles or microbubbles. However, the high shear may damage the microbial cells if the whole broth is recirculated. Even if the cells are filtered via a membrane separation before recirculation, the moving parts, glands, lubricants and sealing fluid of the pump may affect the sterility of the fermenter. Advantages of this system include the production of highly fine and dense microbubbles (100-200 micron), and disadvantages include having moving components which may affect sterility, having a very low volume of air going into system (the ratio of air to liquid flow rate is 1:10), and a high shear inside the pump due to high velocity and pressure.

In a venturi microbubble generator, a venturi nozzle operates using the venturi effect related to the pressure and velocity difference at the throat of the nozzle. The inner surface of the venturi nozzle is designed to create a high vortex through a spiral path which generates very fine microbubbles. The venturi system is suitable for large scale continuous gas fermentation. The liquid is pumped through a pump which has moving parts. The suction of gas is dependent on the vacuum created by the motive liquid. Advantages of this system include: production of microbubbles (less than 200 micron diameter), no moving parts in venturi itself but the system would require a pump. Disadvantages include a requirement for high velocity and high flow rate of liquid (e.g., broth) to generate microbubbles, a possibility that the change in velocity and pressure at the throat of the venturi may induce shear on microbial cells, and a need for several venturi devices to inject a total required volumetric flow rate of gas into the fermenter.

In a sintered block, a porous sparger is made up of sintered glass, ceramics or metal. This type of bubble generator is primarily used on a laboratory scale in non-agitated vessels. Typically throughput of gas is low because of the pressure drop across the sparger. Advantages of this system include the production of a jet of fine microbubbles, and disadvantages include requirements for a gas compressor producing very high pressure gas to generate microbubbles, the possibility of blockage of sparger pores due to fouling, and the need for tedious and time consuming cleaning processes.

Multiple DO Concentration Measurement Points and Control Methods

As described herein, DO concentration may vary through the germination liquid, especially at pressures above atmospheric pressure and/or in a fermenter with minimal to no mechanical agitation. One or more DO concentration measurement points and control methods are used to maintain DO concentration and gaseous oxygen concentration within the limits described herein while maintaining OUR.

Measurements may be taken substantially continuously and used to make future adjustments. In some aspects, measurements are taken at timed intervals. Control loops are included to allow for adjustment to measurements and to allow for more uniform oxygen distribution throughout the fermentation liquid and for the gaseous oxygen concentration in the fermenter headspace. Measurement of DO concentration may be made using continuously measuring DO probes. Measurement of gaseous oxygen in the headspace may be made by any substantially continuous measurement device such as a gaseous oxygen probe or an oxygen analyser (e.g., Raman laser gas analyzer, Gas Chromatographic analyser, micro GC analyzer) having a sufficiently short measurement cycle time to allow headspace oxygen concentration to be continuously controlled below the LOC.

Whether or not there are multiple addition points for the at least one gaseous feed stream comprising oxygen, when non-stirred bioreactors, e.g., fermenters are employed, such as gas-lift external loop fermenters, it is advantageous to measure DO concentration at more than one location (elevation) within the fermenter. DO concentration will typically be the highest near the addition point of the gaseous feed stream comprising oxygen and will then decrease as oxygen and other gaseous feeds (e.g., $CO_2$, $H_2$) react. Each DO concentration should be maintained above a lower control limit that is the minimal DO concentration at which *Cupriavidus necator* shuts down, and below a DO concentration at which oxygen inhibition limits growth and reduces OUR. Furthermore, gaseous oxygen concentration in the headspace gaseous mixture must be maintained below an upper control limit that is a safety factor below the Limiting Oxygen Concentration (LOC) for flammability. It is also advantageous to maintain each measured DO concentration as close as possible to the maximum specific OUR (i.e., maximum oxygen uptake rate per unit mass of biomass in the fermenter).

EXAMPLES

Non-limiting examples which may be useful for understanding the present disclosure are as follows.

Example 1

Figure 2A:
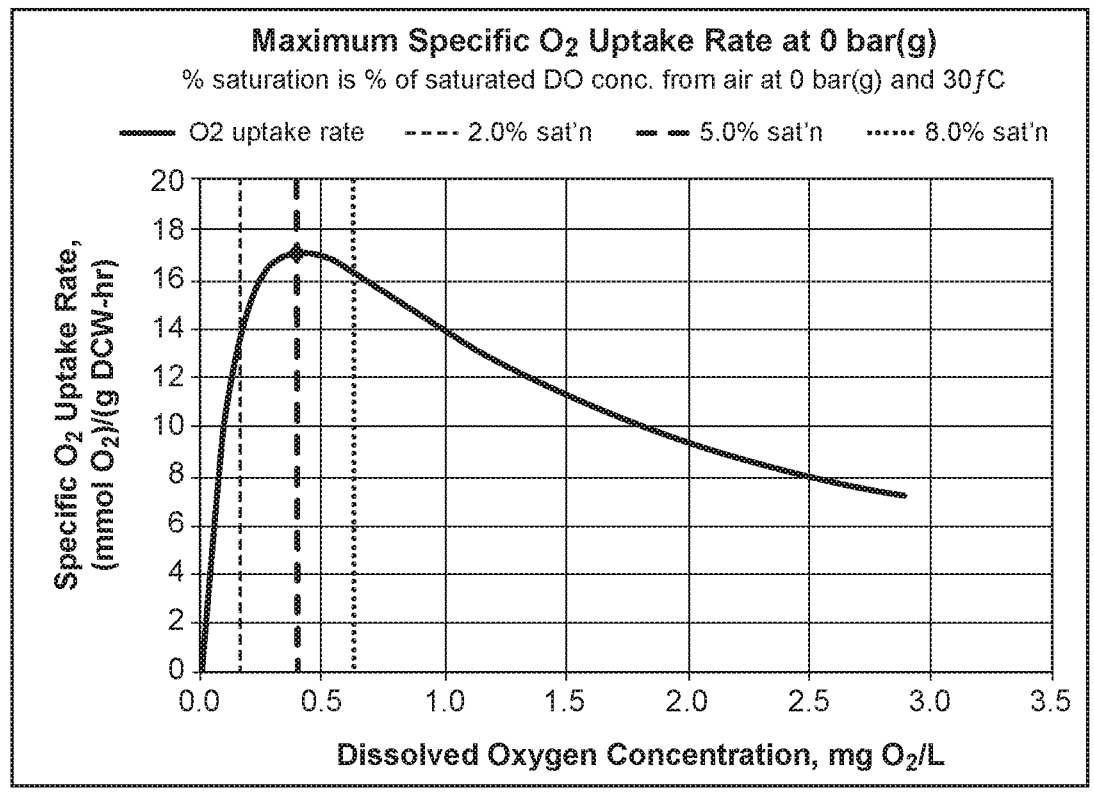
FIGS. 2A and 2B show kinetic models of specificoxygen uptake rate (OUR) vs dissolved oxygen (DO) concentration at different pressures in accordance with embodiments of the present disclosure.
Figure 2B:
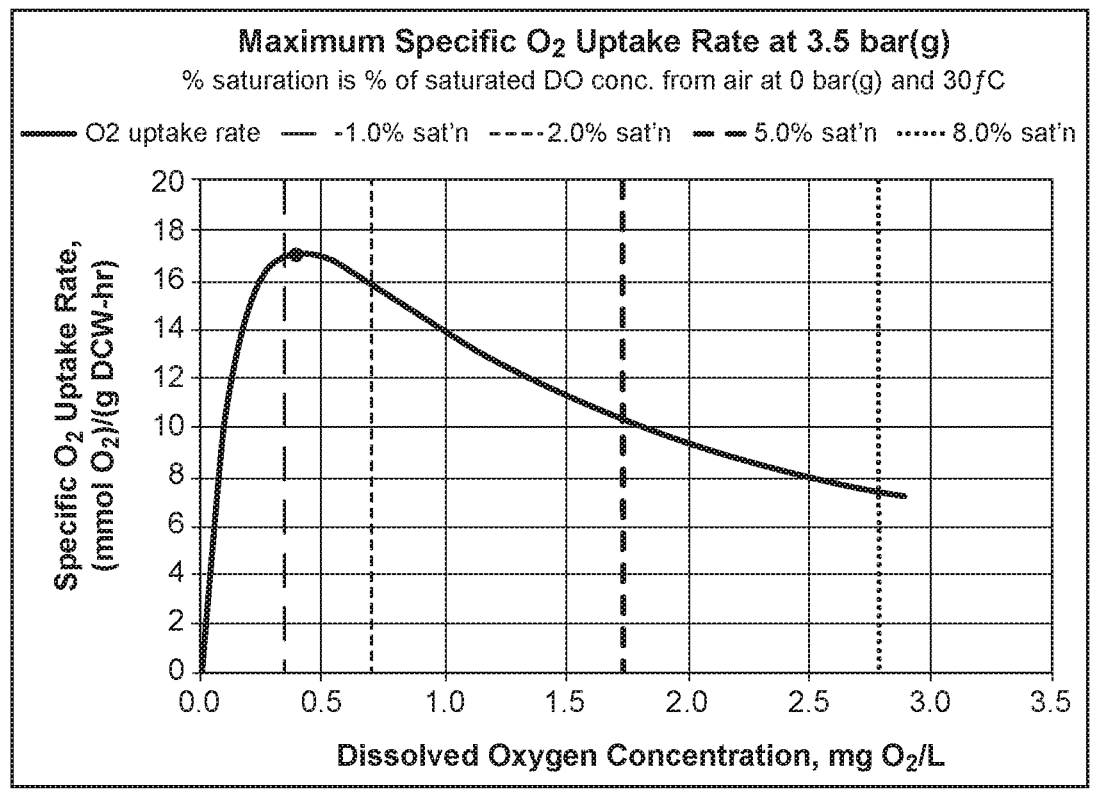

A kinetic model of specific oxygen uptake rate (OUR) vs. dissolved oxygen (DO) concentration for H16 WT *Cupriavidus necator* was prepared and is shown in FIGS. 2a-b. At atmospheric operating pressure (FIG. 2a), the maximum specific OUR occurs at a DO concentration that corresponds to about 5% saturation (based on air at 0 bar(g) and 30° C.). At an elevated operating pressure of 3.5 bar(g) (FIG. 2b), the maximum specific OUR occurs at a DO concentration that corresponds to about 1% saturation (based on air on air at 0 bar(g) and 30° C.), whereas 5% saturation corresponds to a much higher DO concentration and a significantly reduced specific OUR in the oxygen inhibition region to the right of the maximum OUR.

Example 2

Figure 4:
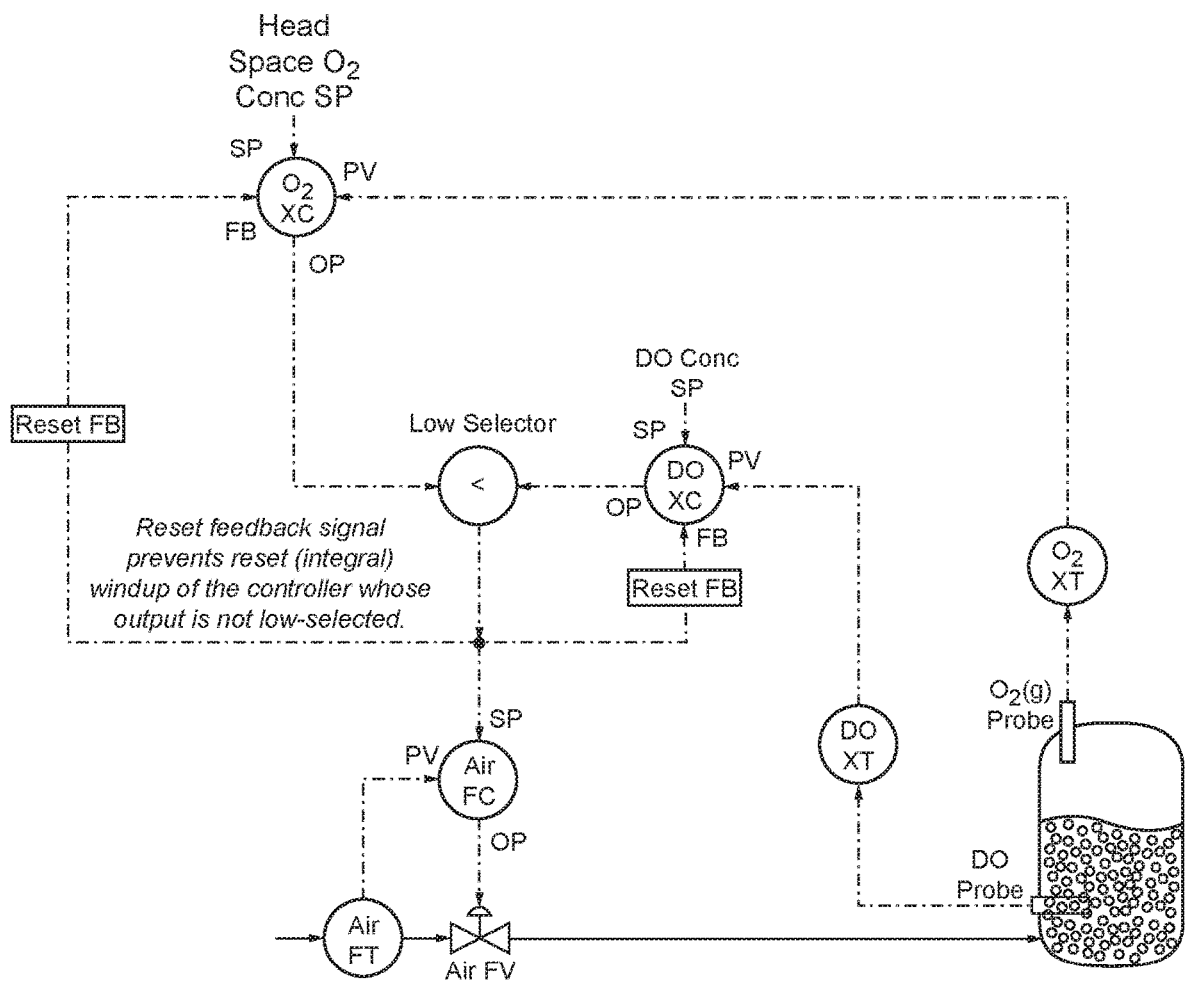
FIG. 4 shows a control method for the DO concentration and for the oxygen concentration in the headspace in accordance with embodiments of the present disclosure.

FIG. 4 shows one control method for headspace oxygen concentration and DO concentration when the at least one gaseous feed stream comprising oxygen is an air feed stream. Air feed flow rate to the fermenter was measured by a flow meter (Air FT) and controlled by an air flow controller (Air FC), such as a Proportional-Integral feedback controller, by regulating an Air flow control valve (Air FV). DO concentration was measured by a DO probe in the fermentation broth. An oxygen probe within the headspace of the fermenter measured the oxygen concentration in the gaseous headspace. A DO concentration controller (DO XC) and a headspace oxygen concentration controller ($O_2$ XC)

competed for control of the Air flow controller set point. The controller that was in control of the Air flow set point was the controller with the lowest output, as determined by the Low Selector. The selected (lowest) Air flow set point was fed back to both the DO concentration controller and the headspace oxygen concentration controller as an anti-reset feedback signal so that the integral action of whichever of the two controller was not in control did not result in controller output "windup" (saturation), thereby enabling that controller to re-gain control whenever its error times proportional gain is such that its output becomes the lower output signal. The headspace oxygen concentration controller set point was set at or below 4 vol % O2 (~70% of the LOC). The DO concentration controller set point was set to a value equal to or below the Transitional DO concentration (at which maximum specific OUR occurs) to ensure operation on the left-side of the specific OUR vs. DO concentration curve.

Example 3

Figure 5:
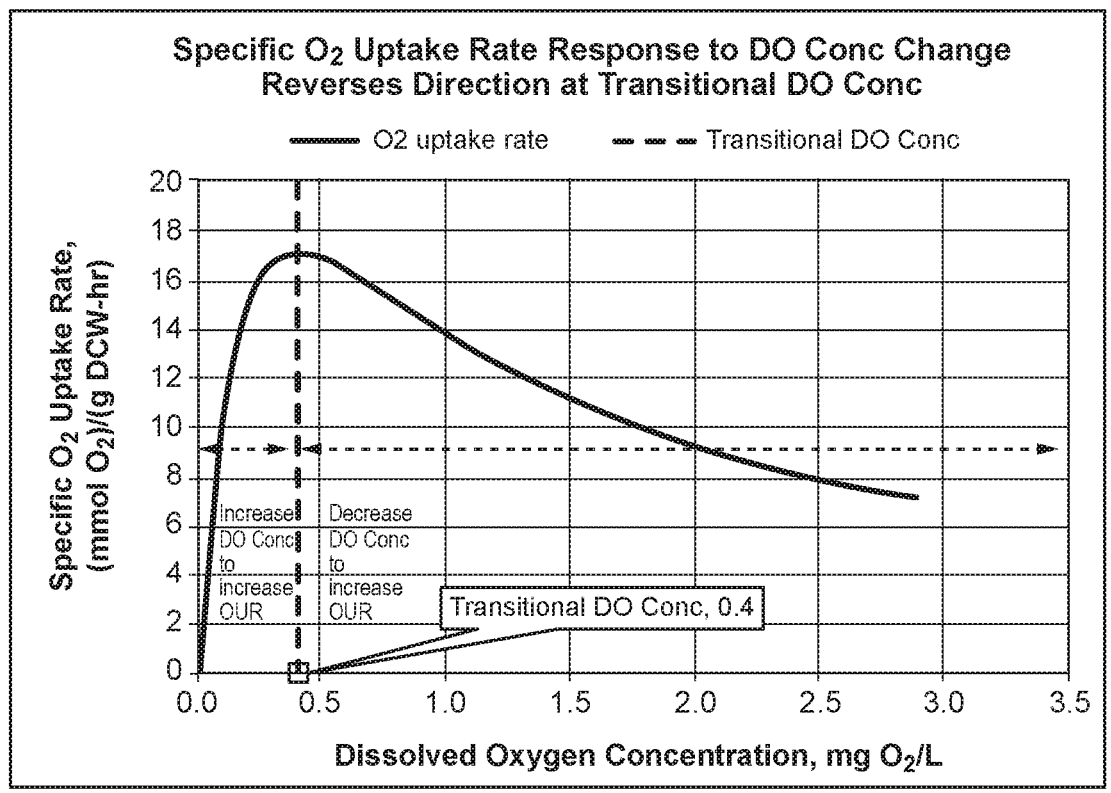
FIG. 5 shows a kinetic model of specific OUR vs. DO concentration for H16 WT *Cupriavidus necator* in accordance with embodiments of the present disclosure.

FIG. 5 shows a kinetic model of specific oxygen uptake rate (OUR) vs. dissolved oxygen (DO) concentration for H16 WT *Cupriavidus necator*. It illustrates that when operating below the Transitional DO concentration, DO concentration must be increased to increase specific OUR and that when operating above the Transitional DO concentration, DO concentration must be decreased to increase specific OUR. The model illustrates that for operation on the left side of the curve, below the Transitional DO concentration at which the maximum specific OUR occurs, increasing the DO concentration will increase the specific OUR, and result in lower residual oxygen concentration (lower headspace oxygen concentration). Conversely, for operation on the right side of the curve, above the Transitional DO concentration, increasing the DO concentration will decrease the specific OUR, and result in higher residual oxygen concentration (higher headspace oxygen concentration). By calculating the specific OUR in real time, the time derivative of specific OUR can be divided by the time derivative of DO concentration to determine whether the change in specific OUR with respect to change in DO concentration is positive (left side of the curve, positive slope) or negative (right side of the curve, negative slope). Because process signals may be noisy, the time derivatives should be filtered such that only true shifts in specific OUR and DO concentration are calculated. An algorithm can then be deployed to maximize the specific OUR by slowly increasing DO concentration setpoint if the calculated slope is positive and slowly decreasing DO concentration setpoint if the calculated slope is negative.

EMBODIMENTS

The following embodiments are contemplated. All combinations of features and embodiment are contemplated.

Embodiment 1

A method for controlling dissolved oxygen concentration in a continuous aerobic gas fermentation process, the method comprising: providing a microorganism to a fermenter; introducing at least two feed streams to the fermenter, wherein at least one feed stream comprises gaseous oxygen and wherein at least one feed stream comprises a flammable gas and optionally oxygen at an oxygen concentration below the limiting oxygen concentration (LOC); measuring the dissolved oxygen concentration in at least one location in the fermenter; measuring the gaseous oxygen concentration in a headspace; and controlling the dissolved oxygen concentration in the fermenter to be greater than a minimum dissolved oxygen concentration required for the microorganism to function and less than the dissolved oxygen concentration above which the gaseous oxygen concentration in the headspace exceeds the limiting oxygen concentration (LOC), wherein the microorganism is considered to function if the microorganism has a specific oxygen uptake rate of at least 1 mmol oxygen/(g dry cell weight)/hour.

Embodiment 2

An embodiment of embodiment 1, wherein the dissolved oxygen concentration is controlled by regulating the oxygen mass transfer rate by regulating at least one of: i. the flow rate of the at least one feed stream comprising gaseous oxygen; ii. the concentration of oxygen in the at least one feed stream comprising gaseous oxygen; iii. the amount of gas holdup as gas bubbles within the fermenter; iv. the size of the gas bubbles within the fermenter; and v. one or more physical properties of the fermentation broth affecting oxygen mass transfer rate.

Embodiment 3

An embodiment of embodiment 2, wherein the flow rate of the at least one feed stream comprising gaseous oxygen is regulated by adjusting the total flow rate of the at least one feed stream comprising gaseous oxygen and/or by adjusting the oxygen concentration in the at least one feed stream comprising gaseous oxygen.

Embodiment 4

An embodiment of any of the embodiments of embodiment 1-3, wherein the flammable gas comprises hydrogen.

Embodiment 5

An embodiment of any of the embodiments of embodiment 1-4, wherein at least one of the at least two feed streams further comprises carbon dioxide.

Embodiment 6

An embodiment of any of the embodiments of embodiment 1-5, wherein the fermenter is selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 7

An embodiment of any of the embodiments of embodiment 1-6, wherein the fermenter is not a stirred fermenter.

Embodiment 8

An embodiment of any of the embodiments of embodiment 1-7, wherein the fermenter is not mechanically agitated.

Embodiment 9

An embodiment of any of the embodiments of embodiment 1-8, wherein the microorganism is dependent on chemoautotrophic metabolism/RUBISCO.

Embodiment 10

An embodiment of any of the embodiments of embodiment 1-9, wherein the microorganism is a RUBISCO-containing microorganism.

Embodiment 11

An embodiment of any of the embodiments of embodiment 1-10, wherein the microorganism is selected from non-pathogenic members of the genera *Ralstonia, Wausteria, Cupriavidus, Alcaligenes, Burkholderia* or *Pandoraea*.

Embodiment 12

An embodiment of any of the embodiments of embodiment 1-11, wherein said microorganism is *C. necator* or *C. metalliduruns*.

Embodiment 13

An embodiment of any of the embodiments of embodiment 1-12, wherein the fermenter is operated at a pressure above atmospheric pressure.

Embodiment 14

An embodiment of any of the embodiments of embodiment 1-13, wherein the method further comprises: measuring gaseous oxygen concentration in a headspace of the fermenter; and controlling the gaseous oxygen concentration in the headspace to be less than 75% of the limiting oxygen concentration (LOC) of the gaseous mixture in the headspace of the fermenter.

Embodiment 15

An embodiment of any of the embodiments of embodiment 1-14, wherein the fermenter comprises at least two oxygen addition inlets.

Embodiment 16

An embodiment of any of the embodiments of embodiment 1-15, wherein the at least one feed stream comprising gaseous oxygen is an air feed stream, an oxygen-enriched air stream, or a pure oxygen stream.

Embodiment 17

A fermenter system for an aerobic gas fermentation process, the system comprising: a fermenter comprising at least two oxygen addition points; a microorganism in the fermenter; and at least two control loops, wherein at least one control loop measures and controls dissolved oxygen content in a fermentation liquid in the fermenter to be greater than a minimum dissolved oxygen concentration required for the microorganism to function, and wherein at least one control loop measures and controls gaseous oxygen concentration in a headspace of the fermenter to not exceed the LOC, wherein the microorganism is considered to function if the microorganism has a specific oxygen uptake rate of at least 1 mmol oxygen/(g dry cell weight)/hour.

Embodiment 18

An embodiment of embodiment 17, wherein the system comprises at least two fermenters in series.

Embodiment 19

An embodiment of embodiment 17 or 18, wherein the system comprises at least two fermenters in parallel.

Embodiment 20

An embodiment of any of the embodiments of embodiment 17-19, wherein the fermenter is selected from the group consisting of a single fermenter, multiple fermenters in series, a membrane fermenter, a fixed-bed fermenter, a fluidized-bed fermenter, a single autoclave, multiple autoclaves in series, a plug flow fermenter, a pneumatically agitated fermenter, a gas-lift fermenter with an external loop having forced-circulation, a bubble-column fermenter, a fixed (packed) bed column fermenter, a horizontal single fermenter with multiple compartments, and multistage column fermenters.

Embodiment 21

An embodiment of any of the embodiments of embodiment 17-20, wherein the fermenter is operated at a pressure above atmospheric pressure.

Embodiment 22

An embodiment of any of the embodiments of embodiment 1-21, wherein the dissolved oxygen concentration is controlled to be at a value below the Transitional DO concentration While the disclosure has been described in detail, modifications within the spirit and scope of the disclosure will be readily apparent to those of skill in the art. It should be understood that aspects of the disclosure and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the disclosure. All US patents and publications cited herein are incorporated by reference in their entirety. References recited herein are provided with full details as follows:

K. T. Klasson, M. D. Ackerson, E. C. Clausen and J. L. Gaddy, "Fermenter Design for Synthetic Gas Fermentations", Fuel (1991), 70, 605-614.

Ishizaki A, Tanaka K, Taga N (2001) Microbial production of poly-D-3-hydroxybutyrate from CO2. Appl Microbiol Biotechnol 57:6-12.

K. Tanaka 1994 Production of Poly-D-3-Hydroxybutyric acid from Carbon Dioxide by a Two Stage Culture Method Employing *Alcaligenes eutrophus* ATCC 17697

Maddipati P I, Atiyeh H K, Bellmer D D, Huhnke R L. Ethanol production from syngas by *Clostridium* strain P11 using corn steep liquor as a nutrient replacement to yeast extract. Bioresoure Technol. 2011 June; 102(11): 6494-501.

Jugder B-E, Chen Z, Ping D T T, Lebhar H, Welch J, Marquis C P. An analysis of the changes in soluble hydrogenase and global gene expression in *Cupriavidus necator* (*Ralstonia eutropha*) H16 grown in heterotrophic diauxic batch culture. Microbial Cell Factories. 2015; 14:42. doi:10.1186/s12934-015-0226-4.

C J Brigham, C S Gai, J Lu, D R Speth, R M Worden, A J Sinskey. Engineering *Ralstonia eutropha* for Production of Isobutanol from $CO_2$, H2 and 02. Advanced Biofuels and Bioproducts (2013) Chapter 39, Springer Science and Business, New York Phillips, J. R.; Huhnke, R. L.; Atiyeh, H. K. Syngas Fermentation: A Microbial Conversion Process of Gaseous Substrates to Various Products. Fermentation 2017, 3, 28.

G W Jones, R E Kenny. Prevention of Gas Explosions by Controlling Oxygen Concentration. Industrial and Engineering Chemistry 1935, 27, 1344-1346.

What is claimed is:

1. A method for controlling dissolved oxygen concentration in a continuous aerobic gas fermentation process, the method comprising:
   a. providing a microorganism to a fermenter connected in series to a second fermenter;
   b. introducing at least three feed streams to the fermenter of a., wherein at least two separate feed streams comprises gaseous oxygen and wherein at least one feed stream comprises a flammable gas and optionally oxygen at an oxygen concentration below the limiting oxygen concentration (LOC);
   c. continuously measuring the dissolved oxygen concentration in at least one location in the fermenter of b to determine wherein the dissolved oxygen concentration must be increased or decreased;
   d. measuring the gaseous oxygen concentration in a headspace in the fermenter of b.; and
   e. controlling the dissolved oxygen concentration in the fermenter to be greater than a minimum dissolved oxygen concentration required for the microorganism to function and less than the dissolved oxygen concentration above which the gaseous oxygen concentration in the headspace exceeds the limiting oxygen concentration (LOC), wherein the microorganism is considered to function if the microorganism has a specific oxygen uptake rate of at least 1 mmol oxygen/(g dry cell weight)/hour, wherein controlling the dissolved oxygen concentration comprises regulating a gas bubble size within the fermenter to be equal to or less than 200 microns,
   f. measuring gaseous oxygen concentration in a headspace of the fermenter following e; and
   g. controlling the gaseous oxygen concentration in the headspace to be less than 75% of the limiting oxygen concentration (LOC) of the gaseous mixture in the headspace of the fermenter, wherein
   the fermenter is operated such that fermentation occurs at a pressure in a range of from 3.5 bar to 7.3 bar;
   a maximum oxygen uptake rate occurs at a dissolved oxygen concentration less than or equal to about 2% saturation,
   at least two control loops are used, wherein at least one control loop measures and controls dissolved oxygen content in the fermentation liquid and wherein at least one control loop measures and controls gaseous oxygen concentration in the headspace of the fermenter,
   the fermenter is a gas-lift external fermenter that is neither a stirred fermenter nor a mechanically agitated fermenter, and comprises an external loop for circulating the fermentation liquid and said microorganism is *Cupriavidus necator* (*C. necator*) or *Cupriavidus metalliduruns*(*C. metalliduruns*).

2. The method of claim 1, wherein the dissolved oxygen concentration is further controlled by regulating the oxygen mass transfer rate by regulating at least one of:
   i. the flow rate of the at least one feed stream comprising gaseous oxygen;
   ii. the concentration of oxygen in the at least one feed stream comprising gaseous oxygen;
   iii. the amount of gas holdup as gas bubbles within the fermenter;
   iv. the gas bubble size within the fermenter to be equal to or less than 100 microns; and
   v. one or more physical properties of the fermentation broth affecting oxygen mass transfer rate, wherein the physical properties are selected from the group consisting of surface tension, viscosity, density, and temperature,
   wherein the oxygen mass transfer rate is regulated by a dissolved oxygen controller.

3. The method of claim 2, wherein the flow rate of the at least one feed stream comprising gaseous oxygen is regulated by adjusting the total flow rate of the at least one feed stream comprising gaseous oxygen and/or by adjusting the oxygen concentration in the at least one feed stream comprising gaseous oxygen.

4. The method of claim 1, wherein the flammable gas comprises hydrogen.

5. The method of claim 1, wherein at least one of the at least two feed streams further comprises carbon dioxide.

6. The method of claim 1, wherein the microorganism is dependent on chemoautotrophic metabolism and RUBISCO.

7. The method of claim 1, wherein the microorganism is a RUBISCO-containing microorganism.

8. The method of claim 1, wherein the fermenter comprises at least two oxygen addition inlets.

9. The method of claim 1, wherein the at least one feed stream comprising gaseous oxygen is an air feed stream, an oxygen-enriched air stream, or a pure oxygen stream.

10. The method of claim 1, wherein the dissolved oxygen concentration is controlled to be at a value below the Transitional DO concentration.

* * * * *